(12) United States Patent
Kuribayashi et al.

(10) Patent No.: US 6,587,717 B1
(45) Date of Patent: Jul. 1, 2003

(54) IONTOPHORESIS DEVICE AND METHOD OF ASSEMBLING THE SAME

(75) Inventors: Mitsuru Kuribayashi, Tsukuba (JP); Hiroyuki Maeda, Tsukuba (JP); Nobuhiro Koga, Tsukuba (JP); Naruhito Higo, Tsukuba (JP)

(73) Assignee: Hisamitsu Pharmaceutical Co., INC, Saga (JP)

( * ) Notice: Subject to any disclaimer, the term of this patent is extended or adjusted under 35 U.S.C. 154(b) by 0 days.

(21) Appl. No.: 09/581,261

(22) PCT Filed: Dec. 21, 1998

(86) PCT No.: PCT/JP98/05775

§ 371 (c)(1),
(2), (4) Date: Jun. 28, 2000

(87) PCT Pub. No.: WO99/33517

PCT Pub. Date: Jul. 8, 1999

(30) Foreign Application Priority Data

Dec. 30, 1997 (JP) ............................................. 9-368648

(51) Int. Cl.⁷ ................................................. A61N 1/30
(52) U.S. Cl. ........................ 604/20; 604/304; 604/306; 604/307; 424/449
(58) Field of Search .................. 604/20, 306, 307, 604/304; 424/449

(56) References Cited

U.S. PATENT DOCUMENTS

| 4,666,441 A | * | 5/1987 | Andriola et al. ............. 604/304 |
| 5,797,867 A | * | 8/1998 | Guerrera et al. .............. 604/20 |
| 5,837,281 A | * | 11/1998 | Iga et al. ..................... 604/304 |
| 5,894,021 A | * | 4/1999 | Okabe et al. ................. 604/20 |
| 5,993,848 A | * | 11/1999 | Suzuki et al. ............... 424/449 |

FOREIGN PATENT DOCUMENTS

EP  1059097  * 12/2000 .................. 604/20

* cited by examiner

Primary Examiner—Thomas Denion
Assistant Examiner—Theresa Trieu
(74) Attorney, Agent, or Firm—Townsend & Banta

(57) ABSTRACT

The present invention relates to an iontophoresis device, which can ensure the long-term stability of a drug and makes the operations for assemblage upon application easy as well as a method of assembling the device. A backing layer (4) is provided with a drug-dissolving portion (11) on a donor electrode-printed portion (6) thereof and a drug support (14) removably contacts with the drug-dissolving portion. A liner (12) is disposed on the backing layer on the skin (40) side and this is peeled off upon practical use. An opening (15) is formed on the liner (12) and an opening (5) is formed on an electrode portion (Ib). When assembling the device, these openings coincide with each other to thus easily and precisely dispose the drug support (14) on the drug-dissolving portion (11).

30 Claims, 13 Drawing Sheets

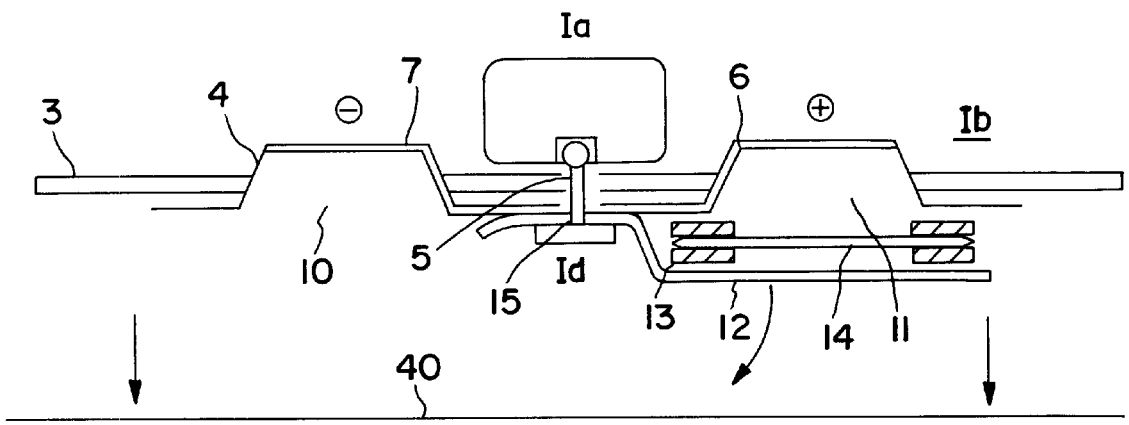
FIG. I
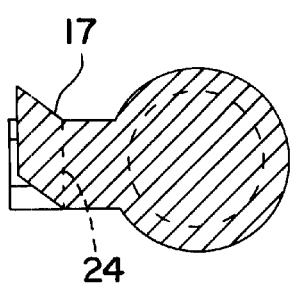
FIG. 2(a)
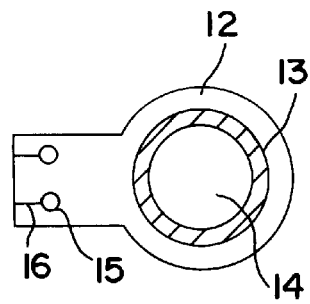
FIG. 2(b)
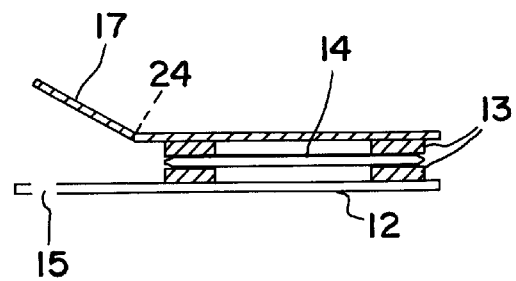
FIG. 2(c)

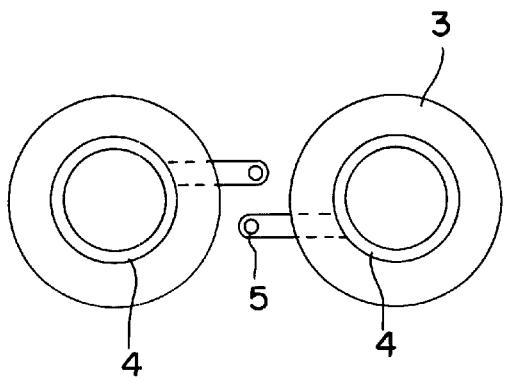
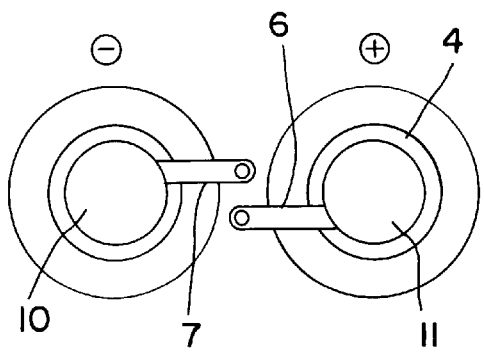
FIG. 5(a)                FIG. 5(b)
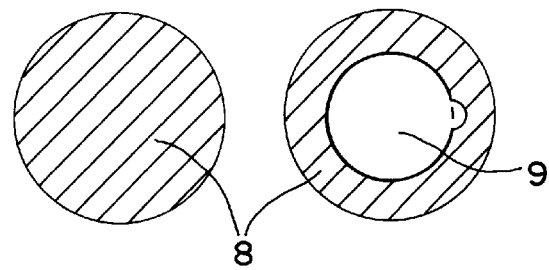
FIG. 5(c)
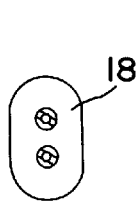
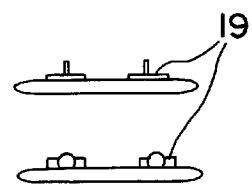
FIG. 6(a)                FIG. 6(b)

IONTOPHORESIS DEVICE AND METHOD OF ASSEMBLING THE SAME

TECHNICAL FIELD

The present invention relates to an iontophoresis device suitable for percutaneous and mucosal applications of drugs and in particular to iontophoresis device of the type, which is activated before practically using as well as a method of assembling the same.

BACKGROUND ART

Recently, there have been developed a variety of dosage forms in the field of pharmaceutical preparations for external use (external pharmaceutical preparations) and the development has gradually become a matter of great concern. The reason for this is as follows: The administration of a drug, which may have a local or systemic pharmacological action, through the skin or the mucous membranes has many advantages. For instance, the sustained-release effect of the drug can be expected; such administration is not greatly influenced by the metabolism due to the first-pass effect in the liver unlike the oral administration and permits the effective use of the drug; and drugs accompanied by, for instance, liver disorders can relatively safely be administered.

However, the normal skin naturally has a protective effect against external stimulations and this makes the absorption and penetration of a drug through the skin relatively difficult. For this reason, in the existing circumstances, a drug is not absorbed in an amount sufficient for ensuring a sufficient effect even if the drug is administered in a dosage form for external use. Moreover, in the administration method, which makes use of absorption routes through biological membrane other than the skin, such as mouth, rectum, oral cavity and nose as well as the sublingual route, it is difficult to penetrate into or transmit through the related biological membrane depending on the kind of drugs and therefore, there have been known a large number of drugs having low bioavailability. Accordingly, there has been desired for the development of an absorption-promoting method, which can sufficiently enhance the permeability, penetrability and absorbency of a drug against the skin and other biological membranes, can ensure a sufficient pharmacological efficacy of the drug and is substantially free of, for instance, its local and systemic toxicity and is highly useful and safe.

As such absorption-promoting methods, there have recently been known, chemically promoting methods, which make use of absorption-promoting agents, and physically promoting methods in which iontophoresis or phonophoresis is employed. Among them, the iontophoresis has unexpectedly attracted special interest recently and has been expected as an administration method, which can solve the foregoing problems.

The iontophoresis is a method for the administration of a drug by applying a voltage to the skin or a mucous membrane to electrically induce the migration of an ionic drug and to thus administrate the drug through the skin or a mucous membrane. In general, an iontophoresis device is provided with a pair of electrodes for iontophoresis, i.e., an anode and a cathode and the device is so designed that these electrodes are arranged on or attached to the skin at a predetermined distance apart from one another and an electric current generated by a current generator is guided to these electrodes to thus carry out treatments.

Moreover, this iontophoresis device has a structure comprising a combination of these electrodes and a layer, which stores a drug therein, and a variety of additives for maintaining the drug efficacy are optionally enclosed in the layer in addition to a predetermined amount of the effective component in order to keep a desired blood concentration in the body over a long period of time.

The iontophoresis device of this type is, for instance, disclosed in Japanese Un-Examined Patent Publication Nos. Sho 62-268569, Hei2-131779, Hei3-268769 and Hei3-45271 and TOKUHYO Nos. Hei 3-504343 and Hei 3-504813.

However, if a drug (such as physiologically active peptides), which suffers from a problem of the solubility in water, is used in these iontophoresis device, the predetermined amount of the drug may be reduced due to the partial decomposition thereof with time. Moreover, if the drug is administered in a high concentration, the drug may be diluted during storing.

If a peptide drug is percutaneously administered by the iontophoresis, it is common that the drug is not maintained in an iso-electric environment, but is kept in an acidic or basic environment. For this reason, the stability of additives, which are incorporated into the device to assist the development of the pharmacological efficacy of the biologically active substance, is greatly influenced by such acidic or basic environment and accordingly, the drug efficacy may be reduced.

Moreover, it has been recognized that when physiologically active peptides are stored in the form of solutions, members constituting the pharmaceutical preparation may be adsorbed on the peripheral site and it is thus quite difficult to maintain a desired concentration of the drug over a long period of time.

As other problems, it has been reported that in a device, which is designed in such a manner that an electrically conductive layer containing a drug in the form of a solution is directly in contact with the electrodes immediately after the electrical charging, the drug is electrolytically decomposed on the electrode surface during electrically charging the device. Accordingly, it would be doubtful whether the decomposed drug through its internal absorption adversely affects the human body.

There have been proposed a variety of methods for the solution of such a problem. For instance, Japanese Un-Examined Patents Publication No. Sho 63-102768 and U.S. Pat. No. 5,310,404 disclose a method, which comprises the steps of arranging a capsule or porch enclosing water or an electrolyte solution above the electrode structure and breaking the capsule or porch immediately before the practical use to thus impregnate the drug-support layer therewith. This method is excellent in that the drug can be stored in a stable condition (dry state), but it is still insufficient since it takes a long time for uniformly permeating the moisture into the whole drug-support layer and the drug efficacy may be reduced due to the dilution of the drug.

In addition, Japanese Patent No. 2,542,792 discloses a method in which a drug-support layer and an electrode layer containing an electrolyte are separately disposed in distinct compartments, which are hinged to one another and then piling one upon another at the hinged portion to thus activate the device. This method permits the improvement in the long-term stability of a drug, but any means for activating the device upon application is not sufficiently devised and therefore, the method may include a lot of causes for artificial errors and cannot achieve sufficiently uniform distribution of the drug after the activation of the device.

Moreover, Japanese Un-Examined Patent Publication No. Hei 3-94771 discloses a device, which is so designed that a selective ion-permeable membrane (such as an ion-exchange membrane) is arranged such that the membrane is adjacent to the skin side of a water-support portion thereof, while a drug is dried and adhered to the side of the selective ion-permeable membrane, which is in contact with the living body, to thus prevent any dilution of the drug and to realize the administration of a trace a mount of the drug to a local site in a high concentration.

Japanese Un-Examined Patent Publication No. Hei 9-201420 discloses a device for iontophoresis, in which an electrode structure layer, a solvent-support layer and a drug-support layer containing a dried physiologically active substance are put in a layer structure in this order and a water-impermeable separator layer is positioned between the solvent-support layer and the drug-support layer. This device is so designed that the solvent-support layer is automatically brought into contact with the drug-support layer by pulling out the separator layer upon activation. This device is quite excellent in that the occurrence of any artificial error is prevented when assembling the device. In this device, however, the solvent-support layer and the drug-support layer are accommodated in the same package, the stability of the drug may be reduced due to any leakage of the solvent from the solvent-support layer and accordingly, it is difficult to ensure the quality of the device. Moreover, even if it were technically possible to completely prevent the leakage of the solvent, the cost required for the development of such a technique would be very high.

As has been described above, there has not yet been developed any iontophoresis device, which can ensure the long-term stability of a drug, can easily and accurately be assembled immediately before the practical use thereof and permits the elimination of any artificial error as much as possible.

Accordingly, it is an object of the present invention to provide an iontophoresis device, which can ensure the long-term stability of a drug and can easily be assembled immediately before the application as well as a method of assembling the device.

Disclosure of the Invention

The foregoing object of the present invention can be accomplished by providing an iontophoresis device, in which an electrode portion equipped with a drug-dissolving portion and a drug portion equipped with a drug-support are provided with alignment structures respectively so that the drug-support and the drug-dissolving portion are brought into contact with one another by coinciding the alignment structure of the drug portions with that of the electrode portion. These alignment structures are, for instance, openings formed on the electrode portion and the drug portion, respectively. These portions can accurately and rapidly be aligned by aligning these openings of the electrode and drug portions with one another.

In addition, the device is also designed in such a manner that an electric current-supply portion is provided with the same alignment structure, the alignment structure is coincided with that of the electrode portion to thus contact the current-supply portion with the electrode portion. The alignment structure for the current-supply portion may be an electrode terminal. In this case, the alignment structure may be formed on the terminal connected to the current-supply portion through a connecting cord.

Alternatively, a connector having the same alignment structure is disposed and the alignment structures of every portions are coincided with one another to thus connect them to the current-supply portion and the connector through the electrode portion. If some of these alignment structures are formed from an electrically conductive material, such alignment structures may be used as electrical connection means.

The drug portion of this iontophoresis device is stored as a package separated from the parts such as those for the current-supply and electrode portions, prior to the practical use. Thus, the device is designed such that the electrode and drug portions are mechanically connected or the electrode and current-supply portions are electrically connected to one another. A means for holding this arrangement used herein is, for instance, electrode terminals of the current-supply portion or conductive snap connector or an auxiliary stand for assemblage. As has been described above, the device according to the present invention may be a set of units in which the electrode portion equipped with an alignment structure and the drug portion equipped with the same alignment structure are separately packaged. In addition, the current-supply portion or the connector having an identical alignment structure and an auxiliary stand for alignment are also packaged separately from the drug portion, in this set of units.

The electrode portion (electrode unit) used herein comprises a member holding a conductive layer, a wiring connected to the conductive layer and an alignment structure formed on at least one of the wiring and the member. The alignment structure is an opening formed on at least one of the wiring and the member. On the other hand, the drug portion (drug unit) comprises a drug-support, a peelable cover for protecting the drug-support and an alignment structure formed on the cover. In this case, the alignment structure is an opening formed on the edge of the cover.

The method of assembling the iontophoresis device according to the present invention comprises the steps of peeling off a cover material disposed on an electrode portion; coinciding an alignment structure of the electrode portion with that of a drug portion to thus dispose a drug-support of the drug portion on a drug-dissolving portion; peeling off a cover of the drug-support on the side of the drug-dissolving portion; and fixing the drug-support to the electrode portion. In this device, a cover is also positioned on the drug-support opposite to the side of the drug-dissolving portion. In this case, however, if an opening is formed on the cover, the assemblage of this device can be completed without peeling off the cover. On the other hand, if any opening is not formed on the opposite cover, the assemblage of the device is completed after peeling off at least part of the cover. More specifically, the opposite cover may completely be peeled off or the part of the cover other than the portion provided with the alignment structure may, for instance, be peeled off.

The electrode portion and the drug portion can be aligned with one another, while making use of the alignment structure disposed on an auxiliary stand, a current-generating portion or a connector. In this case, the both alignment structures of the electrode and drug portions are constituted by openings, while the alignment structure of the auxiliary stand is constituted by an alignment rod capable of being inserted into the opening. On the other hand, the alignment structures for the current-generating portion and the connector may be electrode terminals thereof.

Thus, an iontophoresis device and a method of assembling the same can be provided, which can ensure the long-term stability of a drug, whose assembling operations are easy and accurate upon application and which can eliminate any cause of artificial errors as much as possible.

BRIEF DESCRIPTION OF THE DRAWINGS

FIG. 1 is a diagram showing the cross sectional structure of an iontophoresis device according to the present invention, immediately before the practical use.

FIG. 2 is a diagram showing an embodiment of a drug portion (drug unit), wherein (a), (b) and (c) are a view of the surface, an internal view and a cross sectional view of the drug unit, respectively.

FIG. 5 is a diagram showing an embodiment of the structure of a separate type electrode portion (electrode unit) Ib-2, in which (a), (b) and (c) are a view of the surface, an inner view and a view of the back face of the electrode portion, respectively.

FIG. 6 is a diagram showing an embodiment of the structure of a conductive snap connector Id, in which (a) and (b) are a view of the surface and a cross sectional view thereof, respectively.

BEST MODE FOR CARRYING OUT THE INVENTION

Figure 3A:
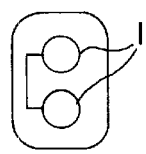
FIG. 3 is a diagram illustrating an embodiment of the structure of a current-generating portion Ia, in which (a), (b) and (c) are a view of the surface, a view of the back face and a cross sectional view of the current-generating portion, respectively.

FIG. 1 is a diagram showing the cross sectional structure of an iontophoresis device according to the present invention, immediately before the practical use. In this figure, every parts are depicted separately to make, easier, the understanding of these parts which are in fact in a laminated relation or come in close contact with one another.

In this figure, a donor electrode-printed portion 6 is positioned on one side of a backing layer 4 and a reference electrode-printed portion 7 is positioned on the other side of the layer 4. An adhesive film 3 such as a medical adhesive tape is disposed on the periphery of the backing layer 4 for securing a pharmaceutical preparation to an application site. The both electrode-printed portions 6 and 7 are connected to a current-generating portion Ia through a conductive snap connector Id. The donor electrode-printed portion 6 on the backing layer 4 is provided with a conductive layer 10 (a drug-dissolving portion) on the donor electrode side, while the reference electrode-printed portion 7 is provided with a conductive layer 10 on the reference electrode side. A drug-support 14 is removably connected to the drug-dissolving portion 11. An adhesive layer 13 is formed on the periphery of the drug-support 14. Thus, the drug-support 14 is fixed to the backing layer 4 or the donor electrode-printed portion 6 through the peripheral adhesive layer 13. On the other hand, a liner 12 is disposed on the peripheral adhesive layer 13 and on the side facing the skin 40.

The liner 12 is peeled off from the iontophoresis device having such a structure upon the practical use and thus the drug-support 14 is exposed. The device, which is in such a condition, is applied to the skin 40. At this stage, the drug, which is in a dry state and supported by the drug-support 14, is dissolved in the water supplied from the drug-dissolving portion 11. Then a power supply for the current-generating portion Ia is switched on to thus put the iontophoresis device in operation.

In this respect, the liner 12 is provided with an opening 15 as a first alignment structure. Moreover, the electrode portion Ib is also provided with an opening 5 as a second alignment structure. In the application of the device, the drug-support 14 can easily and accurately be positioned on the drug-dissolving portion 11 by aligning these openings with one another. At this stage, an electrode terminal of the current-generation portion Ia as a third alignment structure or the connector Id as a fifth alignment structure is inserted into the opening to thus permit rapid positioning operations.

Examples of structures of each part of such an iontophoresis device will be described in more detail below.

FIG. 2 is a diagram showing an embodiment of a drug portion (or drug unit), wherein (a), (b) and (c) are a view of the surface, an internal view and a cross sectional view of the drug unit, respectively. The drug unit Ic of this example is formed by sandwiching a porous drug-support 14 in between a liner 17 on the electrode side, serving as a protective cover, and a liner 12 on the skin side. The liner 17 on the electrode side is provided with a perforation 24 for folding the liner, while the liner 12 on the skin side is provided with two insertion openings 15 for conductive snap connectors as will be detailed below and a perforation 16 for pulling out the liner after the completion of the assemblage. Both of these liners are formed from a film having a low adsorptive affinity for the drug such as polyethylene terephthalate. Moreover, the drug is adhered to and supported on the drug-support 14 by means of, for instance, spray coating or impregnation and then dried. Adhesive layers 13 are arranged on the both sides and the periphery of the drug-support 14 for the purpose of adhesion thereof to the electrode portion and the skin. The adhesive layer 13 is coated on the support in a stripe-like pattern for ensuring ventilation. In this connection, the liners 12 and 17 are subjected to a silicone treatment on the side, which comes in contact with the drug-support 14 in order to prevent any adsorption of the drug and to improve the releasability thereof. Further the liners may likewise be subjected to a treatment for inhibiting any diffusion of a drug solution to the peripheral adhesive layer 13.

Then materials or the like for each part of the drug unit will be described below. The peripheral adhesive layer 13 for the drug-support can be formed by the use of an adhesive as will be detailed below in connection with an adhesive film 3. This layer is formed by pattern coating (such as intermittent coating, stripe coating, intermittent stripe coating) and desirably has a structure through which the air easily passes. The width of the pattern coating is not restricted to any particular one insofar as they can ensure good balance between the adhesion and the air permeability, but the width desirably ranges from 0.1 mm to 20 mm.

The drug-support 14 may be any one insofar as it can support a drug consisting of a physiologically active substance and permits the permeation of the drug therethrough. Moreover, if the drug is a physiologically active peptide or a protein, a hydrophilic porous material may be used, which can support dried drugs and has low adsorptivity. The hydrophilic film formed from such a hydrophilic porous material includes a thin film having high wettability by water such as a hydrophilized hydrophobic (or water-repellent) polymer thin film or a hydrophilic substance-containing hydrophilic polymer film.

Examples of hydrophilic hydrophobic polymer thin films are thin films formed from hydrophilized fluoroplastics (such as hydrophilic DURAPORE available from Millipore Company and hydrophilic poly(tetrafluoroethylene) available from Toyo Roshi Co., Ltd.), thin films such as those formed from hydrophilic polyther sulfone (such as Supor available from Gelman Sciences Inc.) and hydrophilized cellulose derivatives (such as hydrophilized cellulose monoacetate and hydrophilized cellulose triacetate).

Examples of hydrophilic substance-containing hydrophilic polymer thin films include a variety of polymers obtained by adding appropriate surfactants and impregnating therewith and then drying, for instance, hydrophilized cellulose acetate films (such as Asymmetric Ultra Filter available from sartorius Company and cellulose acetate type ones available from Toyo Roshi Co., Ltd.), hydrophilized polycarbonate films (such as Isopore Membranes available from Nihon Millipore Ltd.), hydrophilized poly (tetrafluoroethylene) films (such as Omnipore Membranes available from Nihon Millipore Ltd.), hydrophilized polysulfone films (such as HT Tuffryn available from Gelman Sciences Inc.) and hydrophilized nonwoven fabrics (such as films obtained by coating polyester nonwoven fabrics with cellulose acetate (e.g., coated type membranes available from Toyo Roshi Co., Ltd.)). The hydrophilic films also include, for instance, nylon films (such as Biodyne available from Nihon PALL Ltd.).

Incidentally, drugs unstable to water should desirably be included in or adhered to the drug-support in their dried state in order to improve the stability of these drugs and to inhibit any leakage and deterioration thereof. On the other hand, in case of drugs stable to water, they may be supported on the drug-support in their gel-like conditions. In such a gel-like drug-support, suitably used are water-soluble polymers and hydrogel thereof. A method for preparing such a gel-like drug-support comprises the step of mixing and kneading a gelling agent such as a water-soluble polymer and a drug solution. Moreover, the electrical conductivity of the gel-like drug-support can be enhanced by addition of an electrolyte such as sodium chloride, potassium chloride, sodium carbonate, phosphoric acid or sodium citrate; or a pH-buffering agent such as acetic acid, sodium acetate, phosphoric acid, sodium phosphate, citric acid or sodium citrate. Moreover, the kneaded mixture is formed into a product to such an extent that it has a self shape-maintainability and then spreaded into a sheet or a film. If the kneaded mixture has an insufficient self shape-maintainability, a mesh-like support may be introduced into the gel. The thickness of the gel layer desirably ranges from 0.1 to 2 mm and particularly preferably 0.3 to 0.8 mm. If it is too thin, the gel strength is considerably low, while if it is too thick, the movement of the drug is inhibited and accordingly, the rate of drug absorption is reduced.

The liners 12, 17 as the protective members may be any one insofar as they are formed from a water-impermeable material, but are desirably those capable of being processed through molding (such as thermal molding and vacuum forming). Examples of such water-impermeable materials usable herein are aluminum foils, polyester films, polypropylene films and polyethylene films as well as laminated films thereof. In addition, it is desirable to use these materials after subjecting them to an adsorption-inhibitory treatment such as a treatment with silicone or Teflon. This treatment would facilitate the peeling off thereof from the adhesive layer.

Drugs usable herein are any medicine used in any therapeutic field, which is soluble or dispersible in water and, in particular, physiologically active substances having a molecular weight ranging from $1 \times 10^2$ to $1 \times 10^6$ can widely be used. Examples of drugs are narcotics, analgesics, anorexics, anthelmintics, drugs for asthma, anticonvulsants, antidiarrheals, antineoplastic agents, drugs for Parkinson's disease, antipruritics, sympatholytic agents, xanthine derivatives, drugs for angiocardiac diseases such as calcium channel blockers, antipyretics, β-blockers, antiarrhythmic agents, hypotensive drugs, diuretics, vasodilators for blood vessels including systemic, coronary, peripheral and cerebral vessels, drugs for hemicrania, drugs for drunkness and motion sickness, antiemetics, central nervous system stimulants, drugs for cough and common cold, decogestants, diagnostics, drugs for hormonotherapy, parasympatholytic agents, parasympathomimetic agents, psychostimulants, sedatives, tranquilizers, anti-inflammatory agents, anti-arthritic agents, anti-spasmodics, antidepressants, drugs for treating psychosis, drugs for treating dizziness, anti-anxiety agents, narcotic antagonists, carcinostatic agents, hypnotics, immunosuppressors, muscle relaxants, antiviral agents, antibiotics, anorexics, antiemetics, anti-cholinergic agents, antihistamic agents, contraceptives, antithrombotic agents, bone-absorption suppressors and osteogenesis-promoting agents. However, the present invention is not restricted to these specific drugs. These drugs may be used alone or in any combination.

Specific examples of these drugs include steroids such as estradiol, progesterone, norgestrel, levonorgestrel, norethindrone, medroxy-progesterone acetate, testosterone and esters thereof; nitro group-containing compounds and derivatives such as nitroglycerin and isosorbide dinitrates, nicotine, chlorpheniramine, terfenadine, triprolidine and hydrocortisone; oxicam derivatives such as piroxicam; acetic acid or propionic acid derivatives such as indometacin, flurbiprofen, felbinac and diclofenac, ketoprofen; mucopolysaccharidases such asrthiomucase, buprenorphine, fentanyl, naloxone, codeine, lidocaine, dihydroergotamine, pizotyline, salbutamol and terbutaline; prostaglandins such as misoprostol, enprostil, omeprazole and imipramine; benzamides such as metoclopramine, scopolamine and clonidine; dihydropyridines such as nifedipine, verapamil, ephedrine, pindolol, metoprolol, spironolactone, nicardipine HCl and calcitriol; thiazides such as hydrochilorothiazide and flunarizine; sydnone imines such as molsidomine; sulfated polysaccharides such as heparin fractions and proteins; and peptides such as insulin and homologues thereof; calcitonins and homologues such as elcatonin, protamin and glucagone; globulins, angiotensin I, angiotensin II, angiotensin III, lypressin, vasopressin, somatostatin and homologues thereof; growth hormones and oxytocin; as well as, if necessary, pharmaceutically acceptable salts thereof with acids or bases. Preferred are, for instance, narcotics, hormones, proteins, analgesics, or other low molecular weight cations. More preferably, examples of drugs include peptides or polypeptides such as insulin, calcitonin, calcitonin-related genetic peptides, vasopressin, desmopressin, protirelin (TRH), adrenocorticotropic hormones (ACTH), luteinizing hormone-release hormones (LH-RH), growth hormone-release hormone (GRH), nerve growth factors (NGF) and other release factors, angiotensins, parathyroid hormone (PTH), luteinizing hormone (LH), serumal gonadotropin, hypophyseal hormones (such as HGH, HMG, HCG), growth hormones, somatostatin, somatomedin, glucagon, oxytocin, gastrin, secretin, endorphin, enkephalin, endothelin, cholecystokinin, neurotensin, interferon, interleukin, transferrin, erythropoietin, superoxide dismutase (SOD), filgrastim (G-CSF), vasoactive-intestinal-polypeptides (VIP), muramyl dipeptides, corticotropin, urogastrone and atrial sodium uragogue peptides (h-ANP). However, the present invention is not restricted to these specific drugs. Among these, particularly preferred are peptide hormones. It is also possible to optionally use adsorption-inhibitory agents such as benzalkonium chloride, BSA (bovine serum albumin) and monolauric acid.

In the present invention, at least one of the foregoing drugs and salts thereof may be supported on the drug-support. In addition, the amount of the drug is determined depending on a particular drug in such a manner that upon administration thereof to a patient, a predetermined effective blood concentration is maintained over an effective period of time and the size of the iontophoresis device as well as the area of the drug-delivery surface thereof are determined in proportion thereto.

Figure 3B:
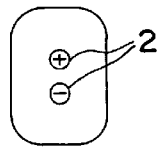
Figure 3C:
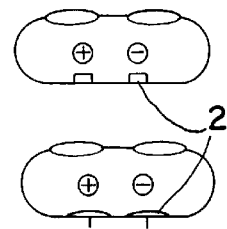
Figure 4A:
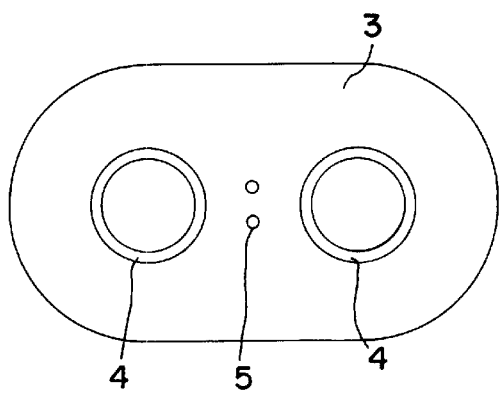
FIG. 4 is a diagram illustrating an embodiment of the structure of an integrated electrode portion (electrode unit) Ib-1, in which (a), (b), (c) and (d) are a view of the surface, an internal view, a view of the back face and a cross sectional view of the electrode portion, respectively.
Figure 4B:
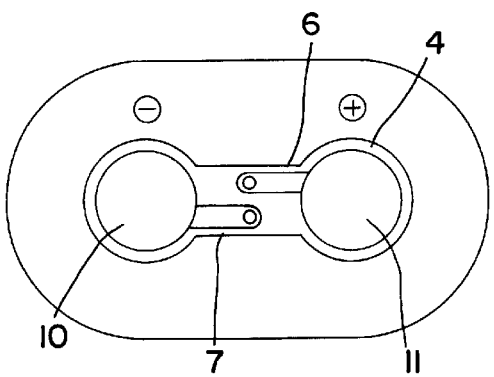
Figure 4C:
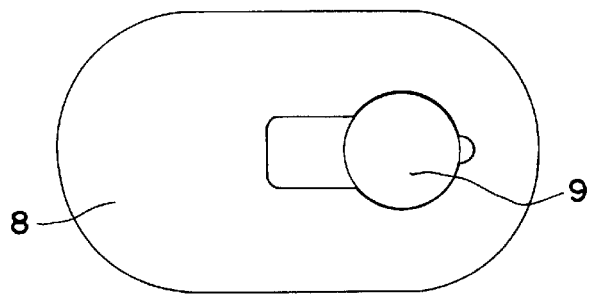
Figure 4D:
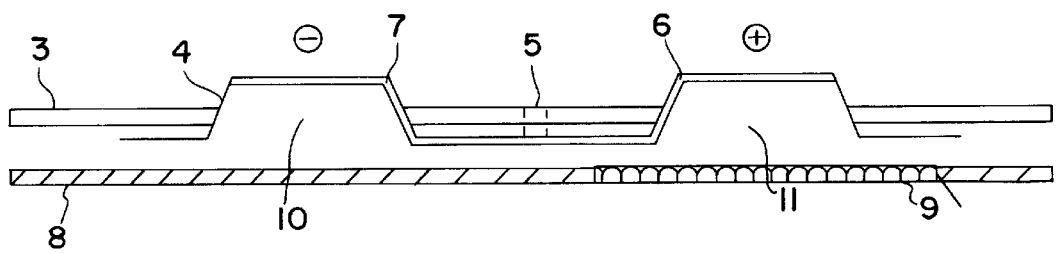

FIG. 3 is a diagram illustrating an embodiment of the structure of a current-generating portion Ia, in which (a), (b) and (c) are a view of the surface, a view of the back face and a cross sectional view of the current-generating portion, respectively. The current-generating portion Ia is a plastic molded body having therein a built-in current-control circuit. A current-control switch 1 is arranged on the current-generating portion, while a female or male electrode terminal 2 (one each of the terminal on the sides of the anode and cathode) is arranged below the current-generating portion. This current-generating portion Ia is preferably designed such that no physical burden due to the size and weight thereof is given to a patient.

More specifically, the current-generating portion is constituted by a self-oscillator circuit provided with a built-in small-sized cell, an appropriate high voltage-generating circuit connected to the oscillator circuit and a control circuit for operating and controlling these circuits. It is also possible to incorporate a BOLUS button for temporarily increasing the injection rate for a drug into the current-generating portion. This is quite useful function when an analgesic is administered to a patient and the patient desires for a temporary increase in the dose thereof in proportion to the degree of his pains.

Moreover, the control circuit is, for instance, designed in such a manner that the circuit permits the manual on/off switching in order to allow the on-demand medication regime and the on/off switching at a period adapted for the biological circadian rhythm and the pattern at intervals of 24 hours. In addition, the control circuit may be equipped with a built-in microprocessor and therefore, the circuit permits the modification of the level of the current and the wave form such as pulses and sinusoidal waves to be applied over a predetermined time. Moreover, the control circuit may comprise a biosensor or a certain kind of feedback system for monitoring the biosignals of a patient, evaluating the treating method and adjusting the amount of the drug to be administered to the patient in response to the results of the evaluation. It is also possible to incorporate one or more programs predetermined by the maker of the drug, a physician or a patient into the control circuit.

FIG. 4 is a diagram illustrating an embodiment of the structure of an integrated electrode portion Ib-1, in which (a), (b), (c) and (d) are a view of the surface, an internal view, a view of the back face and a cross sectional view of the electrode portion, respectively. The integrated electrode portion Ib-1 has a backing layer 4 consisting of a film of a polyolefin such as polyester or polypropylene or a molded body of such a film laminated with an aluminum layer. Printed electrode portions 6, 7 are arranged on the molded backing layer 4 and they are formed by printing silver (on the anode side) and silver chloride (on the cathode side). Moreover, two insertion openings 5 (one each of the opening on the sides of the anode and cathode) for conductive snap connectors are positioned on the printed electrode portion at the center of the backing layer.

Conductive layers 10, 11 are formed on the integrated electrode portion Ib-1 in such a manner that they are adjacent to the printed electrode portions 6, 7 and the material used for forming these layers is a water-retentive material such as a nonwoven fabric or a hydrophilic polymer, which comprises an electrolyte. In this respect, the conductive layer 11 on the donor side (in this example, the layer on the anode side) also serves as a moisture supply source for the drug accommodated in the drug portion Ic upon activation. Moreover, the conductive layers are packaged with a water-impermeable cover material 9 through easily peeled heat seal in order to prevent any moisture evaporation during storage. Further an adhesive film 3 such as a medical adhesive tape is applied onto the periphery of the backing layer 4 for the purpose of fixing the pharmaceutical preparation to a drug-application site and a liner 8 is fitted to the adhesive film during storage.

FIG. 5 is a diagram showing an embodiment of the structure of a separate type electrode portion Ib-2, in which (a), (b) and (c) are a view of the surface, an internal view and a view of the back face of the electrode portion, respectively. The separate type electrode portion Ib-2 has a backing layer 4 consisting of a film of a polyolefin such as polyester or polypropylene or a molded body of such a film laminated with an aluminum layer. Printed electrode portions 6, 7 are arranged on the molded backing layer 4 and they are formed by printing silver (ion the anode side) and silver chloride (on the cathode side). Moreover, an insertion opening 5 for each conductive snap connector is positioned on the printed electrode portion 6, 7.

Conductive layers 10, 11 are formed on the separate type electrode portion Ib-2 in such a manner that they are adjacent to the printed electrode portions 6, 7 and the material used for forming these layers is a water-retentive material such as a nonwoven fabric or a hydrophilic polymer, which comprises an electrolyte. In this respect, the conductive layer 11 on the donor side (in this example, the layer on the anode side) also serves as a moisture supply source for the drug accommodated in the drug portion Ic upon activation. Moreover, the conductive layers are packaged with a water-impermeable cover material 9 through easily peeled heat seal in order to prevent any moisture evaporation during storage. Further an adhesive film 3 such as a medical adhesive tape is applied onto the periphery of the backing layer 4 for the purpose of fixing the pharmaceutical preparation to a drug-application site and a liner 8 is fitted to the adhesive film during storage.

Incidentally, these electrode portions may have a known electrode structure. For instance, usable herein are materials such as platinum black, titanium, carbon, aluminum, iron, lead, carbon-containing conductive rubber and conductive resins, with platinum electrodes, silver electrodes, silver chloride electrodes or the like being particularly desirable.

In addition, the cover material 9 is not restricted to any particular one insofar as it is formed from a water-impermeable material. For instance, the cover material is formed from a film laminated with an aluminum layer. If a highly sealed condition by heat sealing is required, the cover material is laminated with a plurality of films such as those described above in connection with the liner or it is coated with another polymer resin. This makes the peeling off of the cover material easy. For instance, there can be used an easily peelable laminate film. It is desirable that the laminate film have a peel strength at 180 degrees of not more than 2000 g.

A pressure-sensitive adhesive is used as an adhesive material for the adhesive film 3 (the adhesive layer 13 at the periphery of the drug support). Any pressure-sensitive adhesive maybe used herein insofar as they can maintain the iontophoresis device on the surface of the skin or mucous membrane of a patient, while the device is brought into close contact therewith, they have an adhesive force sufficient for ensuring good adhesion of the drug support to the drug-dissolving portion and they are physiologically acceptable for the skin. Specific examples thereof are acrylic adhesives comprising homopolymers or copolymers of alkyl acrylates whose alkyl moiety has 4 to 18 carbon atoms, such as acrylic acid, methyl acrylate, ethyl acrylate, 2-ethylhexyl acrylate, isooctyl acrylate, decyl acrylate, lauryl acrylate and stearyl acrylate; methacrylic adhesives comprising homopolymers or copolymers of alkyl methacrylates whose alkyl moiety has 4 to 18 carbon atoms, such as methyl methacrylate, ethyl methacrylate, butyl methacrylate, 2-ethylbexyl methacrylate, isooctyl methacrylate, decyl methacrylate, lauryl methacrylate and stearyl methacrylate; silicone, type adhesives such as those comprising polyorganosiloxane and polydimethyl-siloxane; and rubber type adhesives such as those comprising natural rubber, polyisobutylene, polyvinyl ether, polyurethane, polyisobutylene, polybutadiene, styrene-butadiene copolymer, styrene-isoprene copolymer and styrene-isoprene-styrene block copolymer. Moreover, the adhesive material may, if necessary, comprise a tackifier and a softening agent.

A material for the backing layer 4 herein used may be an effective component-impermeable material. Examples thereof are films, sheets and foams of synthetic resins such as polyethylene, polypropylene, polyethylene terephthalate, polyvinyl chloride, polyvinylidene chloride, plasticized vinyl acetate copolymer, plasticized vinyl acetate-vinyl chloride copolymer, polyamide, cellophane, cellulose acetate, ethyl cellulose, polyester, polycarbonate, polystyrene, polyurethane, polybutadiene, polyimide, polyacrylonitrile, polyisoprene, polystyrene derivatives, ethylene-vinyl acetate copolymer, ethylene-polyvinyl alcohol copolymer, fluoroplastics, acrylic resins, epoxy resins, which may be used alone or in the form of a laminate of at least two of them.

In addition, the films, sheets, foams or the like of these synthetic resins may be laminated with metal foils such as aluminum and tin foils; nonwoven fabrics and synthetic paper or may be covered with deposited aluminum layers and ceramic coatings. Moreover, if closed package by, for instance, heat sealing is required, they may be laminated with a heat-sealable material.

The electrode portion may be deposited on the backing layer by, for instance, a method comprising the steps of mixing an electrode material with, for instance, a print ink for electric wirings, applying the print ink to a material for the backing layer and then drying the same; a method comprising the steps of spreading an electrode material and then fixing the material to the backing layer; a method comprising the step of depositing an electrode material onto the backing layer; or a method in which the electrode portion is formed by photo-etching an electrode material applied onto the backing layer. In addition, an insulating layer may additionally be applied onto a part of the printed electrode layer, which may come in contact with the skin of a patient.

The conductive layer may simply comprise water or may comprise at least one member selected from the group consisting of soft porous materials such as ion-exchangeable polymers, foaming materials and sponge and water-absorptive polymers. Moreover, the conductive layer may comprise an electrolyte such as sodium chloride, potassium chloride, sodium carbonate, phosphoric acid or sodium citrate; or a pH-buffering agent such as acetic acid, sodium acetate, phosphoric acid, sodium phosphate, citric acid or sodium citrate, for the improvement of the electric conductivity thereof.

Specific examples of the preferably used conductive layer in general include nonwoven fabric, paper, gauze, absorbent wadding, polyethylene or polypropylene having open cells, polyvinyl acetate, porous films and foams of, for instance, polyolefin foams, polyamide foams and polyurethane, natural polysaccharides such as karaya gum, tragacanth gum, xanthane gum, starches, gum arabic, locust bean gum, gellan gum, guar gum and carrageenan; gelatin, pectin, agar, sodium alginate or polyvinyl alcohol and partially saponified products thereof; polyvinyl formal, polyvinyl methyl ether and copolymers thereof; polyvinyl pyrrolidone and copolymers thereof; aqueous or water-soluble cellulose derivatives such as sodium carboxymethyl cellulose, methyl cellulose, hydroxyethyl cellulose, hydroxymethyl cellulose, hydroxypropyl methyl cellulose, hydroxypropyl cellulose and cellulose acetate phthalate; carboxyvinyl polymer, polyacrylamide and polyacrylamide derivatives, casein, albumin, chitin, chitosan, polyacrylic acid, sodium polyacrylate, poly-HEMA, poly-HEMA derivatives, methoxyethylene-maleic anhydride copolymer, N-vinyl acetamide, N-vinyl acetamide and acrylic acid and/or acrylic acid salt copolymers, as well as crosslinked products thereof, water-soluble polymers optionally plasticized with, for instance, ethylene glycol or glycerin and hydrogels thereof. However, the present invention is not restricted to these specific ones. In addition, the foregoing materials may be used in combination of at least two of them. Moreover, it is also possible to use, if necessary, benzalkonium chloride, BSA (bovine serum albumin) and adsorption-inhibitory agent such as monolauric acid.

Furthermore, the conductive layer may also comprise an ion-exchangeable polymer for the removal of ions competitive with a desired drug. Such an ion-exchangeable polymer usable herein is appropriately selected from anion-exchange polymer, cation-exchange polymer or ampholytic ion-exchange polymer, depending on the ionic properties of each particular drug. In addition, the ion-exchangeable polymer may be incorporated into the conductive layer by, for instance, a method comprising the step of dispersing fine powder of an ion-exchangeable polymer in the foregoing polymer to thus form the mixture in a gel-like form or a method, which makes use of a product of such an ion-exchlangeable polymer previously formed into a film, but the present invention is not restricted to these methods at all.

The capacity of the conductive layer on the donor electrode side (drug-dissolving portion) is not particularly restricted to a specific range, but depends on, for instance, the size of the electrode portion and the optimum amount of water required for dissolving a drug accommodated in the drug portion, or the water content of the absorptive member of the drug-dissolving portion. In this respect, however, if the amount of water is too large, it may cause leakage of the drug-dissolving liquid, while if it is too small, the drug present in the drug portion cannot completely be dissolved and the drug efficacy is correspondingly reduced. Therefore, the amount of water is desirably on the order of the maximum water absorption of the drug support. If a hydrogel is used in the drug-dissolving portion, the syneresis thereof particularly preferably ranges from 10 to 100 mg/cm$^2$. Moreover, the hydrogel should have such a gel strength that the gel is never broken during the assemblage of the device and during the application thereof to the skin and therefore, the hydrogel desirably has a gel strength ranging from 400 to 1500 g/cm$^2$.

The amount of water required for dissolving a drug present in the drug support is in advance controlled in the drug-dissolving portion. Thus, a precise amount of water can certainly and rapidly be supplied to the drug support at any time upon practical use and this makes the therapeutic effect accurate. Moreover, this can also simplify the treating operations and reduce the treating time.

FIG. 6 is a diagram showing an embodiment of the structure of a conductive snap connector Id, in which (a) and (b) are a view; of the surface and a cross sectional view thereof, respectively. This connector Id is provided with two electrode terminals 19 (male and female) on an electrode terminal-fixing table 18 and they are designed in such a manner that they can be connected to the electrode terminals 2 (female and male) of the current-generating portion Ia after the assemblage of the device.

The current-generating portion Ia is connected to the electrode portion Ib such that the latter is sandwiched between the electrode terminal on the side of the current-generating portion and that on the side of the conductive snap connector Id. The electrode terminal on the conductive snap connector side comes in contact with the printed electrode portion (either of the anode and cathode) of the electrode portion due to the connection. Accordingly, the current-generating portion and the electrode portion can electrically be charged and the electrical connection can thus be established.

In addition, if they are connected, while inserting the drug portion upon the assemblage of the device, the electrode terminal also serves as a means for mechanical connection for the purpose of positioning or aligning the electrode portion with the drug portion. Thus, the electrode terminals of the current-generating portion and the conductive snap connector are important as means for assembling the device.

In respect of the modes of the connection of the current-generating portion to the electrode portion, the device may be operated in a cordless mode or a remote control mode using a cord. In case of the former, a small-sized current-generating portion is directly connected to the electrode portion when it is intended to carry out an easy and quick treatment. Besides, in case of the latter, the current-generating portion is connected to the electrode portion through an exclusive connecting cord when it is intended to carry out a treatment while operating the device at hand. In this connection, connection means are fitted to the both sides of the connecting cord for connecting the current-generating portion to the conductive snap connector.

In this embodiment, electrode terminals (both anode and cathode terminals) are incorporated into a plastic molded body so that it serves to connect the terminals, to each other, of the current-generating portion and the conductive snap connector. In this respect, the connection means is not restricted to an electrode terminal and the shape and the connection mode thereof may arbitrarily be changed. Preferably, the connection means on the conductive snap connector side has such a structure that the drug portion and the electrode portion are in line with each other and they can firmly maintain a desired arrangement.

Figure 7A:
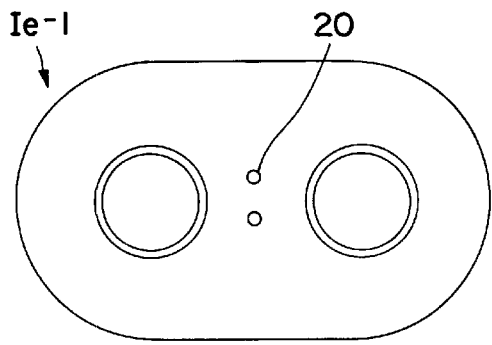
FIG. 7 is a diagram showing an embodiment of the structure of an auxiliary stand for assemblage Ie-1, wherein (a) and (b) are a view of the surface and a cross sectional view, respectively.
Figure 7B:
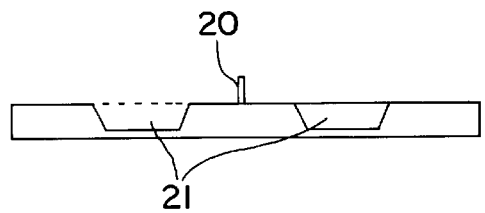

FIG. 7 is a diagram showing an embodiment of the structure of an auxiliary stand for assemblage Ie-1, wherein (a) and (b) are a view of the surface and a cross sectional view, respectively. The auxiliary stand for assemblage Ie-1 is designed in such a manner that it possesses a space 21 for accommodating the electrode portion, whose shape corresponds to that of the backing layer 4 of the electrode portion and that it has two rods 20 as a sixth alignment structure used for positioning upon the assemblage of the device. Materials for the auxiliary stand for assemblage are not restricted to any specific one insofar as they are those capable of being shaped and/or processed such as paper, metals, wood and plastic films (such as polypropylene, Teflon and polyvinyl chloride films), but preferred are plastic films having high shape-retention ability and a thickness of not less than 0.5 mm.

This auxiliary stand for assemblage is devised to make, easy, the operations required when a patient assemble this device. In this embodiment, the stand is provided with a space 21 for accommodating the electrode portion, whose shape corresponds to that of the backing layer 4 of the electrode portion and therefore, the electrode portion can be disposed on the precise position on the auxiliary stand. The electrode-accommodating space 21 is also important in that it can prevent any damage of the electrode portion possibly encountered when the device is assembled.

In addition, the alignment rod 20 makes it easy to align the electrode portion with the drug portion upon the assemblage of the device and is effective for eliminating the occurrence of any artificial error.

Figure 8A:
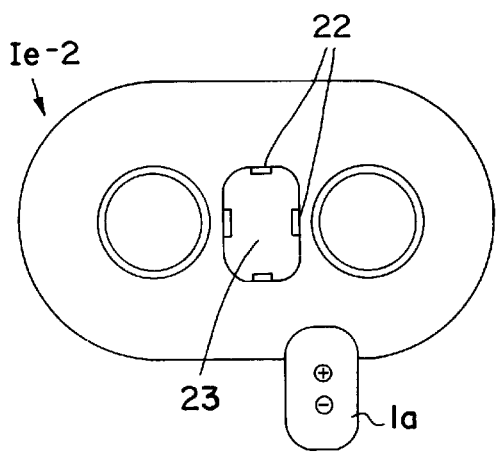
FIG. 8 is a diagram showing an embodiment of the structure of an auxiliary stand for assemblage Ie-2, wherein (a) and (b) are a view of the surface and a cross sectional view, respectively.
Figure 8B:
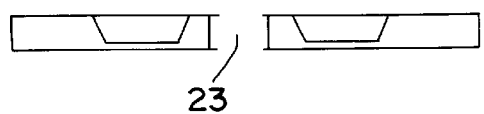

FIG. 8 is a diagram showing an embodiment of the structure of an auxiliary stand for assemblage Ie-2, wherein (a) and (b) are a view of the surface and a cross sectional view, respectively. The auxiliary stand for assemblage Ie-2 is designed so as to have a space 23 for accommodating the current-generating portion, whose shape is in conformity with that of the current-generating portion Ia. The space 23 is provided with a means 22 for fixing the current-generating portion to the auxiliary stand Ie-2.

Figure 9A:
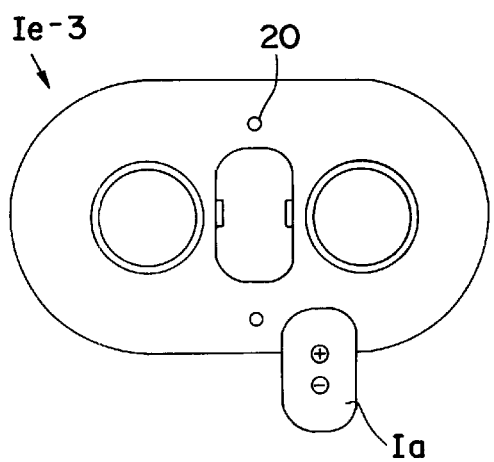
FIG. 9 is a diagram showing an embodiment of the structure of an auxiliary stand for assemblage Ie-3, wherein (a) and (b) are a view of the surface and a cross sectional view, respectively.
Figure 9B:
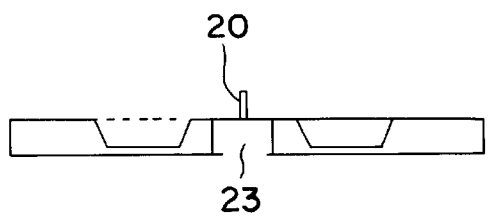

FIG. 9 is a diagram showing an embodiment of the structure of an auxiliary stand for assemblage Ie-3, wherein (a) and (b) are a view of the surface and across sectional view, respectively. The auxiliary stand for assemblage Ie-3 is designed so as to have a space 23 for accommodating the current-generating portion, whose shape is in conformity with that of the current-generating portion Ia and two alignment rods 20. The functions of the alignment rods 20 and the space 23 are the same as those discussed above in connection with the foregoing auxiliary stand.

Figure 10A:
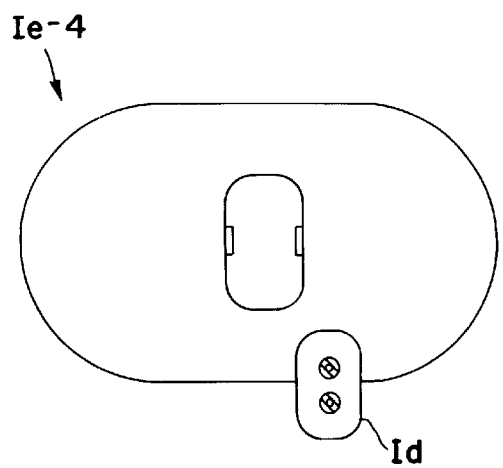
FIG. 10 is a diagram showing an embodiment of the structure of an auxiliary stand for assemblage Ie-4, wherein (a) and (b) are a view of the surface and a cross sectional view, respectively.
Figure 10B:
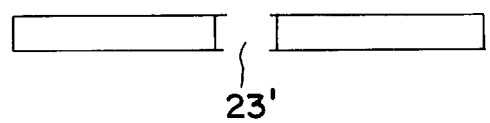

FIG. 10 is a diagram showing an embodiment of the structure of an auxiliary stand for assemblage Ie-4, wherein (a) and (b) are a view of the surface and across sectional view, respectively. The auxiliary stand for assemblage Ie-4 is provided with a space 23' for accommodating the conductive snap connector Id, whose shape is adapted for that of the connector. The function of the space 23' is the same as that described above in connection with the foregoing space 23.

In this connection, the auxiliary stand for assemblage may have a structure combined with those described above depending on the shape and the procedures for assemblage of the device and the shape thereof can further be modified. Materials for the auxiliary stand for assemblage are not restricted to any specific one insofar as they are those capable of being shaped and/or processed, such as paper, metals, wood and plastic films (such as polypropylene, Teflon and polyvinyl chloride films), but preferred are plastic films having a high shape-retention ability and a thickness of not less than 0.5 mm.

Figure 11A:
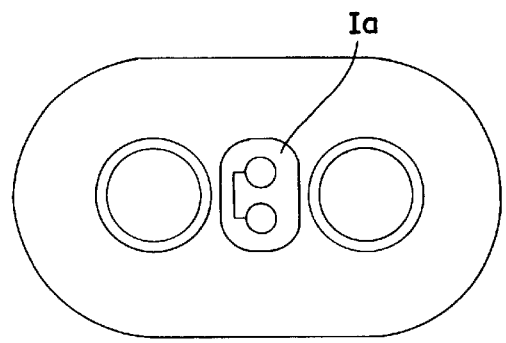
FIG. 11 is a diagram showing the configuration of an iontophoresis device in which the integrated electrode portion Ib-1 is incorporated according to the present invention after the completion of its assemblage, wherein (a) and (b) are a view of the surface and a view of the back face of the device, respectively.
Figure 11B:
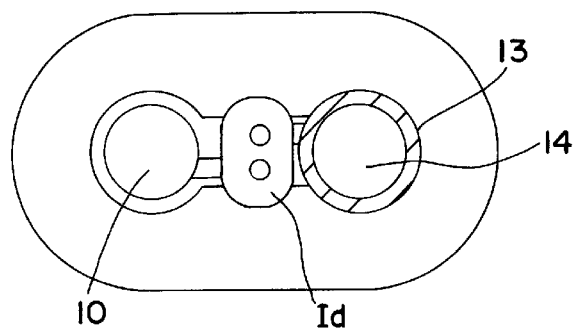

FIG. 11 is a diagram showing the configuration of an iontophoresis device, in which the integrated electrode portion Ib-1 is incorporated, according to the present invention, after the completion of its assemblage, wherein (a) and (b) are a view of the surface and a view of the back face of the device, respectively. As will be seen from this figure, a current-generating portion Ia is disposed on the surface of the electrode portion and a conductive snap connector Id is disposed on the back face thereof. Thus, the electrode portion is fixed to and sandwiched between the current-generating portion Ia and the conductive snap connector Id.

Figure 12A:
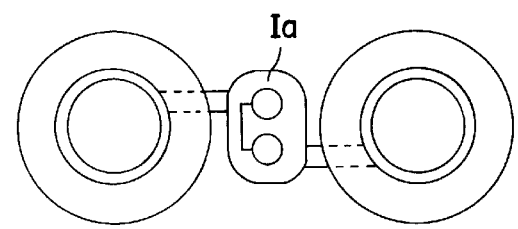
FIG. 12 is a diagram showing the configuration of an iontophoresis device in which the separate type electrode portion Ib-2 is incorporated according to the present invention after the completion of its assemblage, wherein (a) and (b) are a view of the surface and a view of the back face of the device, respectively.
Figure 12B:
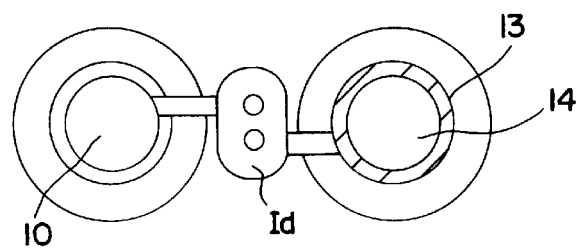

FIG. 12 is a diagram showing the configuration of an iontophoresis device, in which the separate type electrode portion Ib-2 is incorporated, according to the present invention, after the completion of its assemblage, wherein (a) and (b) are a view of the surface and a view of the back face of the device, respectively. In this embodiment, a current-generating portion Ia is disposed on the surface of the wirings connected to the electrode portion, while a conductive snap connector Id is arranged on the back face thereof. Thus, the wirings are fixed to and sandwiched between the current-generating portion Ia and the conductive snap connector Id.

Figure 13A:
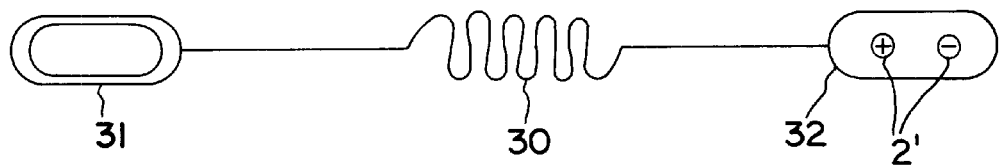
FIG. 13 is a diagram showing an embodiment in which the current-generating portion Ia is connected to the electrode portion through a connecting line 30, wherein (a), (b) and (c) are a connecting cord, a view of the surface and a view of the back face, respectively.
Figure 13B:
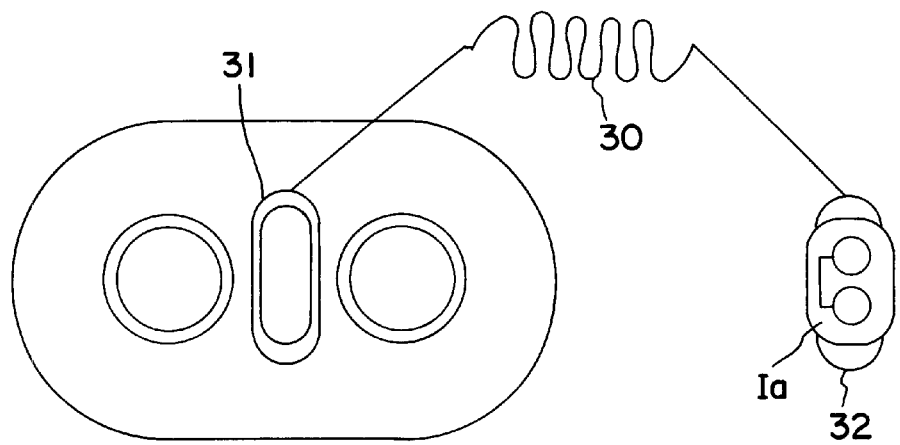
Figure 13C:
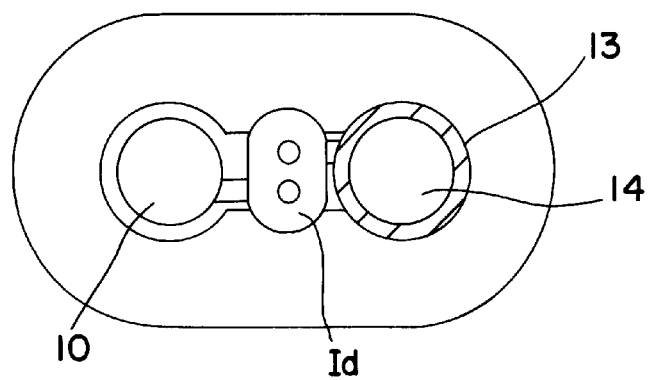

FIG. 13 is a diagram showing an embodiment, in which the current-generating portion Ia is connected to the electrode portion through a connecting line 30, wherein (a), (b) and (c) are a connecting cord, having a fourth alignment structure and a view of the surface and a view of the back face of the device, respectively. In case of this embodiment, a cord-connecting portion 31 (on the side of the electrode portion), as the fourth alignment structure which is connected to one end of the connecting cord, is arranged on the surface of the device and a conductive snap connector Id is arranged on the back face of the device. Thus, the electrode portion is fixed to the device by the cord-connecting portion 31 (on the side of the electrode portion) and the conductive snap connector. A cord-connecting portion 32 (on the side of the current-generating portion) is disposed on the other end of the connecting line 30 and thus the cord-connecting portion is connected to the current-generating portion. The cord-connecting portion 32 (on the current-generating portion side) is equipped with an electrode terminal 2'. The use of this connecting cord permits the operations of this device at a place distant apart from the device.

Now, we will hereunder explain Examples of the method of assembling the iontophoresis device using these component parts.

EXAMPLE 1

FIG. 14 is a diagram illustrating an embodiment of the method of assembling an iontophoresis device, which makes use of an integrated electrode, in which (a) shows assembling processes and (b) shows a process in which the auxiliary stand Ie-4 for assemblage is used.

Figure 14A:
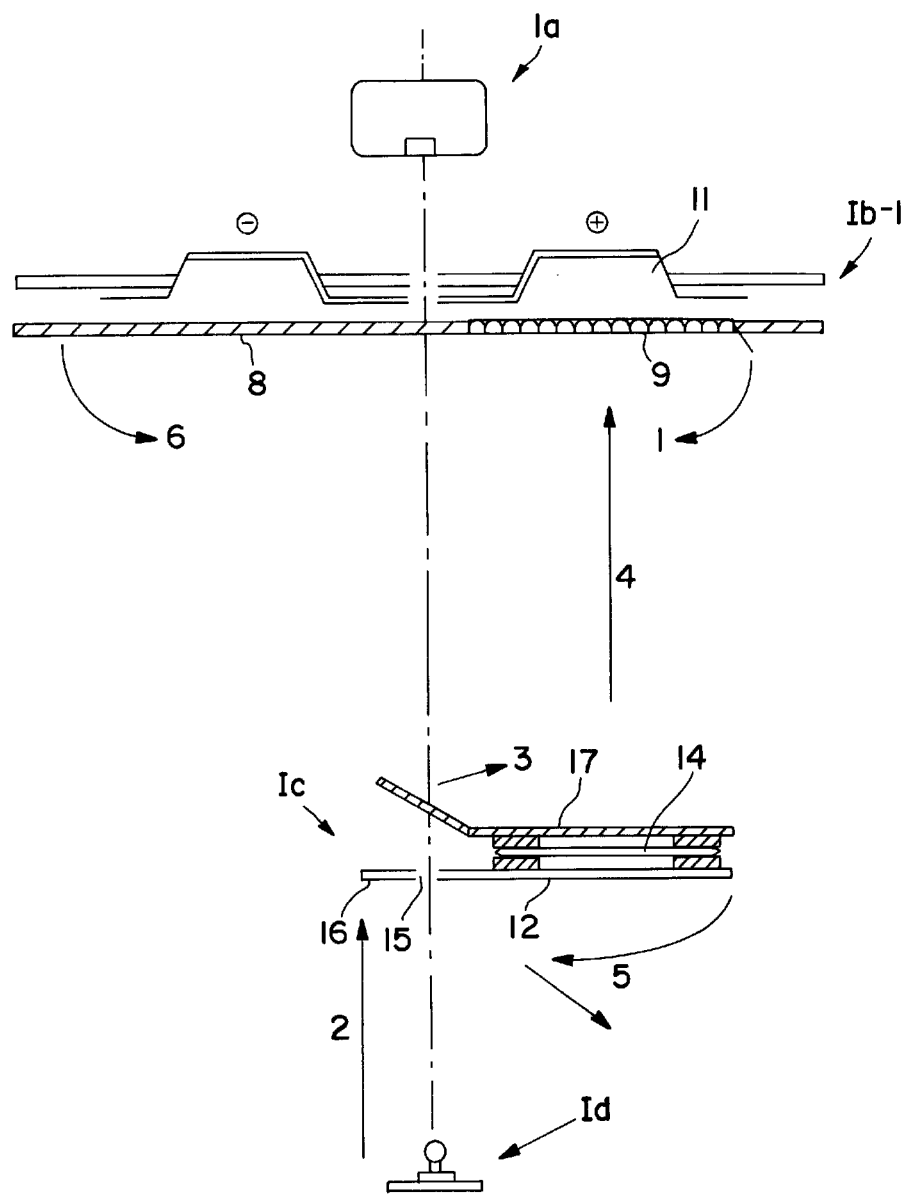
FIG. 14 is a diagram illustrating an embodiment of the method of assembling an iontophoresis device, which makes use of an integrated electrode, in which (a) shows assembling processes and (b) shows a process in which the auxiliary stand Ie-4 for assemblage is used.

As shown in FIG. 14 (a)$\hat{1}$, a cover material 9 of an integrated electrode portion is first peeled off to thus expose a drug-dissolving portion 11. Then a current-generating portion Ia, a drug portion Ic and the integrated electrode portion Ib-1, which are independent and separated from one another, are put in order using a conductive snap connector Id so that the integrated electrode and the drug portion are in line with each other and arranged and in contact with each other, as shown in FIG. 14(a)$\hat{2}$. Next, a liner 17 of the drug portion on the electrode portion side (which has been folded along a perforation) is peeled off as shown in FIG. 14(a)$\hat{3}$. Subsequently, a drug support 14 of the drug portion is connected to the drug-dissolving portion 11 of the integrated electrode portion as shown in FIG. 14(a)$\hat{4}$. Thus the moisture present in the drug-dissolving portion 11 penetrates into the drug support 14 so that the drug is dissolved and activated. Thereafter, a liner 12 of the drug portion on the skin side is pulled out from the conductive snap connector Id as shown in FIG. 14(a)$\hat{5}$. Further a liner 8 for an adhesive film is peeled off as shown in FIG. 14(a)$\hat{6}$. At this stage, the device can be applied to an affected part of a patient to thus initiate the treatment thereof. In this regard, the liner 12 of the drug portion on the skinside is provided with a perforation 16 for pulling out the same through insertion openings 15 (two portions) for the conductive snap connector as shown in FIG. 2 and accordingly, the liner can easily be pulled out.

Figure 14B:
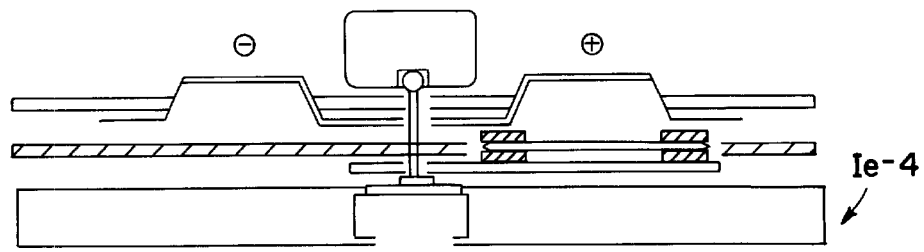

In this Example, the device can likewise be assembled using the auxiliary stand Ie-4 for assemblage as shown in FIG. 14(b). The iontophoresis device according to this Example permits the improvement of the long-term stability of a drug and easy and precise operations for assemblage. Thus the device permits the elimination of any artificial error as much as possible and the supply of water required for the dissolution of the drug to the drug support in high precision. Moreover, the conductive snap connector simultaneously serves as a means for aligning the electrode portion and the drug portion and a means for electrically connecting the electrode portion to the current generating portion and therefore, the device can easily be applied to any application site of a patient after the assemblage thereof.

EXAMPLE 2

FIG. 15 is a diagram illustrating another embodiment of the method of assembling an iontophoresis device, which makes use of an integrated electrode, in which (a) shows the first half of the assembling process and (b) shows the second half of the process, respectively.

Figure 15A:
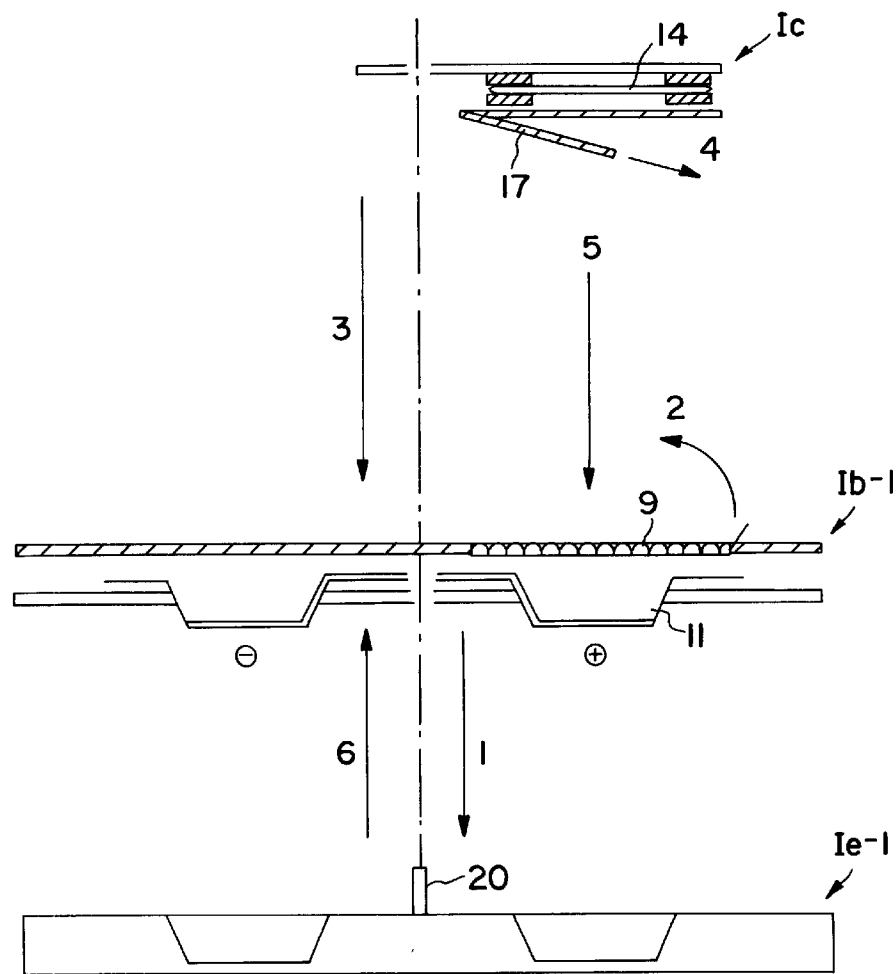
FIG. 15 is a diagram illustrating another embodiment of the method of assembling an iontophoresis device, which makes use of an integrated electrode, in which (a) shows the first half of the assembling process and (b) shows the second half of the process, respectively.

An electrode portion is positioned using an alignment rod 20 of an auxiliary stand Ie-1 for assemblage as shown by an arrow $\hat{1}$ in FIG. 15(a) and then a cover material 9 of the electrode portion Ib-1 is peeled off as indicated by an arrow $\hat{2}$ in FIG. 15(a) to thus expose a drug-dissolving portion 11. Then a drug portion Ic and the electrode portion Ib-1 are arranged and in contact with one another using the alignment rod 20 while they are in line with each other, as indicated by an arrow $\hat{3}$ in FIG. 15(a). Subsequently, a liner 17 of the drug portion Ic on the electrode portion side (which has been folded along a perforation) is peeled off as indicated by an arrow $\hat{4}$ FIG. 15(a), whereby a drug support 14 of the drug portion can easily be connected to the drug-dissolving portion 11 of the integrated electrode portion as indicated by an arrow $\hat{5}$ in FIG. 15(a). The moisture present in the drug-dissolving portion 11 penetrates into the drug support 14 and thus the drug is dissolved and activated. Thereafter, the pharmaceutical preparation is detached from the auxiliary stand as indicated by an arrow $\hat{6}$ in FIG. 15(a).

Figure 15B:
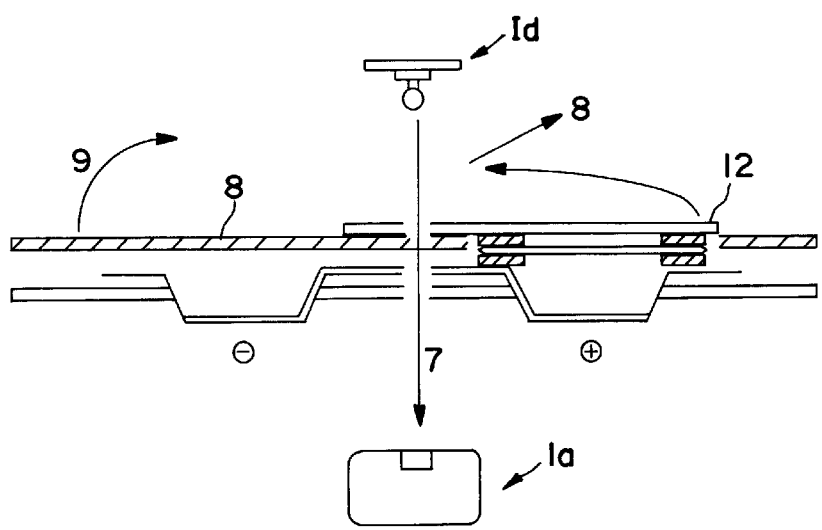

Then a conductive snap connector Id and a current-generating portion Ia are disposed in the same configuration used in Example 1 as indicated by an arrow $\hat{7}$ in FIG. 15(b). After pulling out a liner 12 of the drug portion on the skin side immediately before the application of the device to the skin as indicated by an arrow $\hat{8}$ in FIG. 15(b), a liner 8 for an adhesive film is peeled off as shown by an arrow ⑨ in FIG. 15(b). At this stage, the device can be fitted to an application site of a patient to thus initiate the treatment. The iontophoresis device according to this Example makes the assemblage thereof upon application easier and more accurate and therefore, it permits the elimination of any artificial error as much as possible and the supply of water required for the dissolution of the drug to the drug support in high precision.

EXAMPLE 3

FIG. 16 is a diagram illustrating a further embodiment of the method of assembling an iontophoresis device, which makes use of an integrated electrode, in which (a) shows the first half of the assembling process and (b) shows the second half of the process, respectively.

Figure 16A:
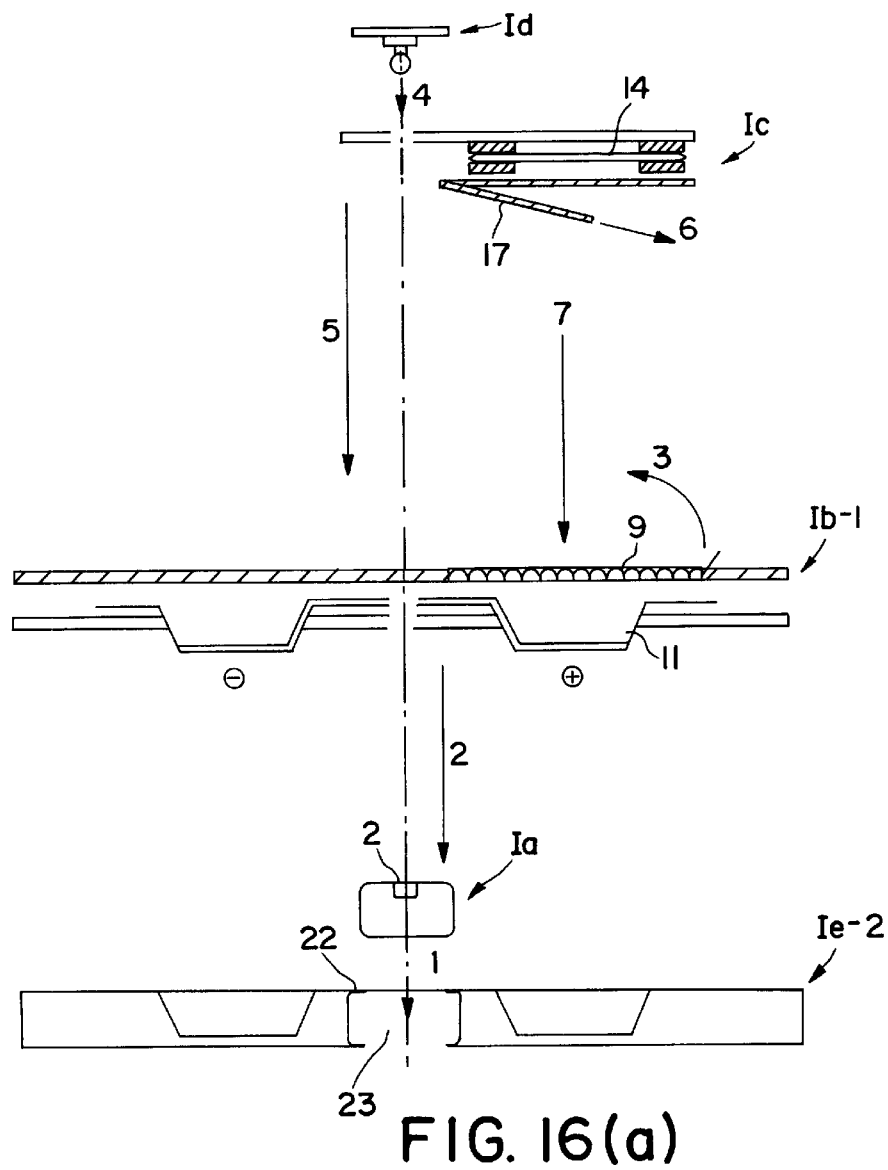
FIG. 16 is a diagram illustrating a further embodiment of the method of assembling an iontophoresis device, which makes use of an integrated electrode, in which (a) shows the first half of the assembling process and (b) shows the second half of the process, respectively.

A current-generating portion Ia is incorporated into a space 23 for accommodating the current-generating portion on an auxiliary stand Ie-2 for assemblage so that an electrode terminal 2 (female) looks upward as indicated by an arrow $\hat{1}$ in FIG. 16(a) and fixed to the stand by means 22 for fixing. Then an electrode portion Ib-1 is disposed while it coincides with a recess of the auxiliary stand Ie-2 as indicated by an arrow $\hat{2}$ in FIG. 16(a) and thereafter a cover material 9 of the electrode portion Ib-1 is peeled off to thus expose a drug-dissolving portion 11 as indicated by an arrow $\hat{3}$ in FIG. 16(a). Subsequently, the electrode portion Ib-1 is brought into contact with a drug portion Ic using a conductive snap connector Id as indicated by arrows $\hat{4}$ and $\hat{5}$ in FIG. 16(a) in such a manner that they are in line with each other and thereafter a liner 17 of the drug portion Ic on the electrode portion side (which has been folded along a perforation) is peeled off as indicated by an arrow $\hat{6}$ in FIG. 16(a). Then a drug support 14 of the drug portion is connected to the drug-dissolving portion 11 of the integrated electrode portion as shown by an arrow $\hat{7}$ in FIG. 16(a), whereby the moisture present in the drug-dissolving portion 11 penetrates into the drug support 14 and the drug is thus dissolved.

Figure 16B:
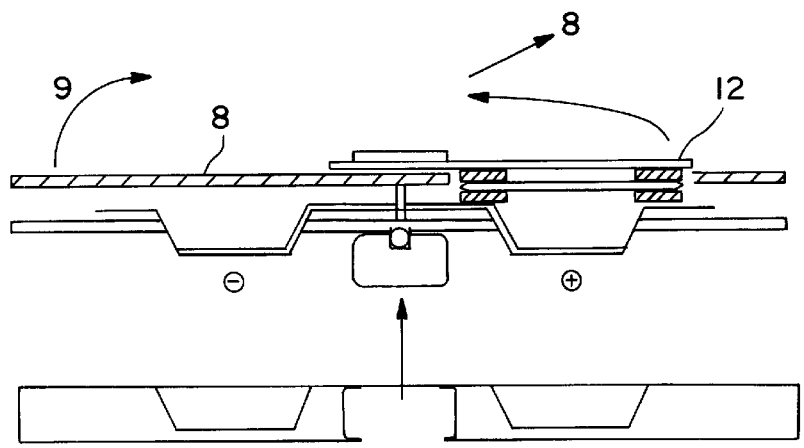

Thereafter a liner 12 of the drug portion on the skin side is pulled out from the conductive snap connector Id as indicated by an arrow $\hat{8}$ in FIG. 16(b), then a liner 8 for an adhesive film is peeled off immediately before the application of the device as indicated by an arrow $\hat{9}$ in FIG. 16(b) and finally the device is detached from the auxiliary stand. Thus, the iontophoresis device can be applied to an application site without any pre-treatment to thus initiate the treatment. The iontophoresis device according to this Example makes the assemblage thereof upon application easier and more accurate and therefore, it permits the elimination of any artificial error as much as possible and the supply of water required for the dissolution of the drug to the drug support in high precision.

EXAMPLE 4

FIG. 17 is a diagram illustrating an embodiment of the method of assembling an iontophoresis device, which makes use of a separate type electrode, in which (a) shows the first half of the assembling process and (b) shows the second half of the process, respectively.

Figure 17A:
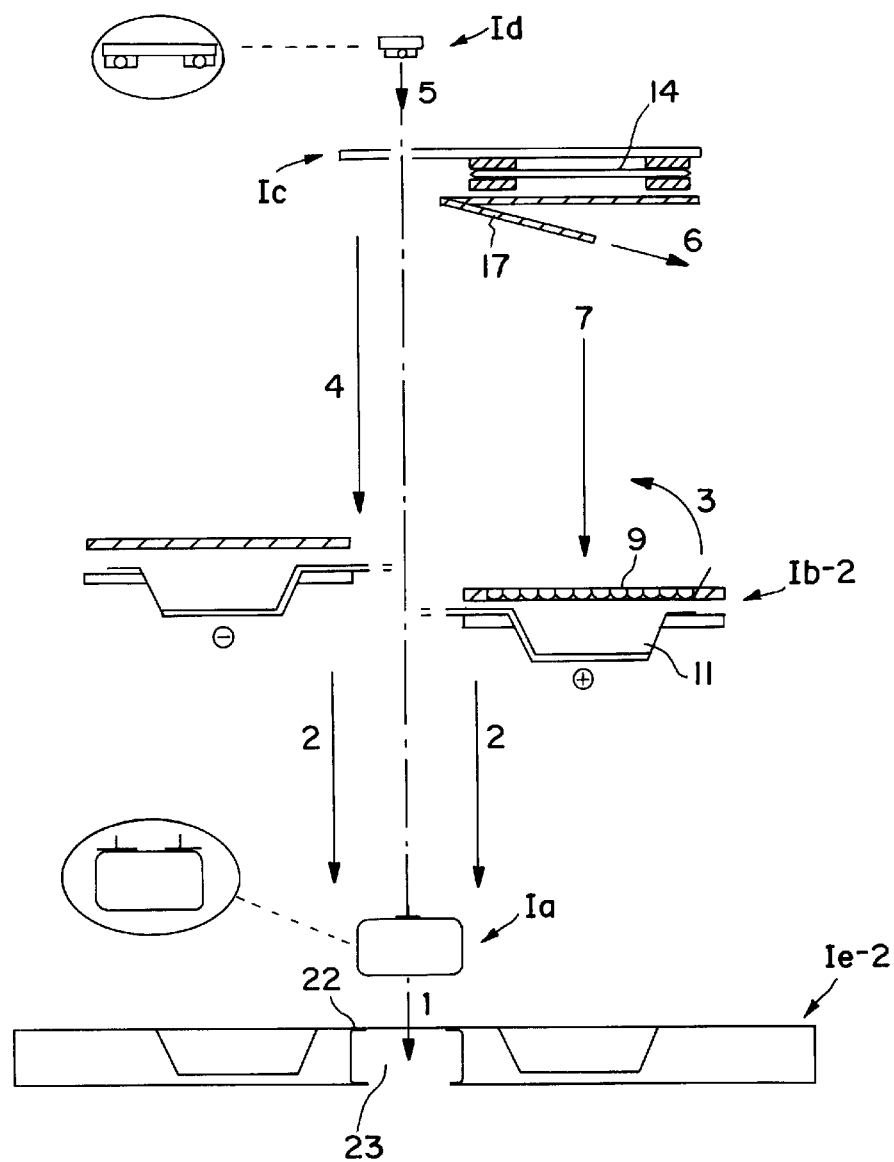
FIG. 17 is a diagram illustrating an embodiment of the method of assembling an iontophoresis device, which makes use of a separate type electrode, in which (a) shows the first half of the assembling process and (b) shows the second half of the process, respectively.

First of all, a current-generating portion Ia is incorporated into a space 23 for accommodating the current-generating portion on an auxiliary stand Ie-2 for activation in such a manner that two electrode terminals (male) look upward, as indicated by an arrow $\hat{1}$ in FIG. 17(a). Then the current-generating portion Ia is fixed to the auxiliary stand Ie-2 by a fixing means 22 as shown by an arrow $\hat{2}$ in FIG. 17(a). Next, electrode portions Ib-2 (anode and cathode portions) are disposed on the auxiliary stand Ie-2 such that each of the portions coincides with a recess on the stand. Thereafter, a cover material 9 on the electrode portion is peeled off to thus expose a drug-dissolving portion 11, as indicated by an arrow $\hat{3}$ in FIG. 17(a). The cover material 9 of the electrode portion can be peeled off after a drug portion and the electrode portion are put on top each other, on the auxiliary stand. Subsequently, the electrode portion Ib-2 is brought into contact with the drug portion Ic using a conductive snap connector Id in such a manner that these portions are in line with each other, as indicated by arrows $\hat{4}$ and $\hat{5}$ in FIG. 17(a) and then a liner 17 of the drug portion on the electrode portion side (which has been folded along a perforation) is peeled off as indicated by an arrow 6 in FIG. 17(a). Then a drug support 14 of the drug portion is connected to the drug-dissolving portion 11 of the separate type electrode portion as shown by an arrow 7 in FIG. 17(a). As a result, the moisture present in the drug-dissolving position 11 penetrates into the drug support 14 and the drug therein is dissolved and activated.

Figure 17B:
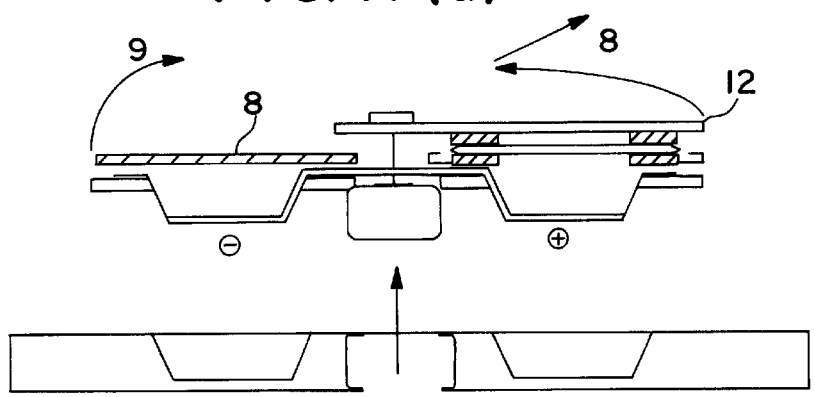

Then a liner 12 of the drug portion on the skin side is pulled out from the conductive snap connector as shown by an arrow 8 in FIG. 17(b) and thereafter, a liner 8 for an adhesive film is peeled off immediately before the application of the device, as shown by an arrow 9 in this figure. Finally, the device is removed from the auxiliary stand. At this stage, the device can be fitted to an application site to thus initiate a treatment.

In this respect, the order of the procedures for assembling the device is not restricted to that described above and may be hanged depending on the mode of usage thereof by a patient, while taking measures suited to the occasion. For instance, the device may have a structure in which a bonding function is imparted to the cover material 9 of the electrode portion and the cover material is peeled off and pulled out. Moreover, it is also possible that the device is not removed from the auxiliary stand, while the latter is used as an auxiliary means for fitting the device to an application site and then the stand is removed from the device after the completion of the application. As has been discussed above, the iontophoresis device according to this Example permits, at a time, the achievement of the integration of the electrode portion (anode and cathode portions), precision of activation (positioning) and operability after the activation (easy handling ability) by the use of the conductive snap connector and the current-generating portion. Accordingly, the device can sufficiently show the desired functions. Moreover, the electrode portion can separately and independently be produced and therefore, the separate type electrode portion is superior to the integrated electrode portion in production facilities and quality control.

COMPARATIVE EXAMPLE 1

Figure 18A:
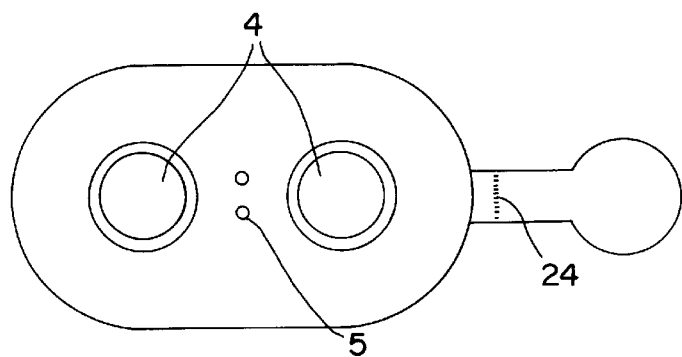
FIG. 18 is a schematic diagram showing an iontophoresis device as a comparative example, in which (a), (b) and (c) are a view of the surface, views of the inner portion and back face and a cross sectional view of the device, respectively.
Figure 18B:
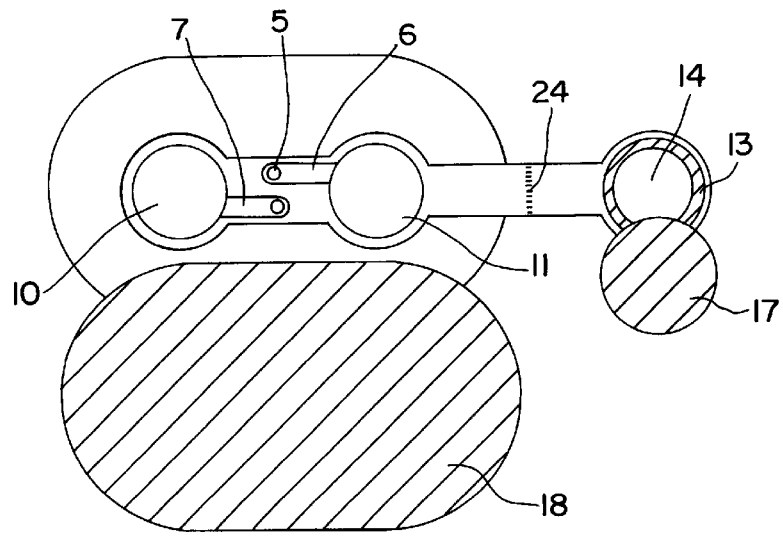
Figure 18C:
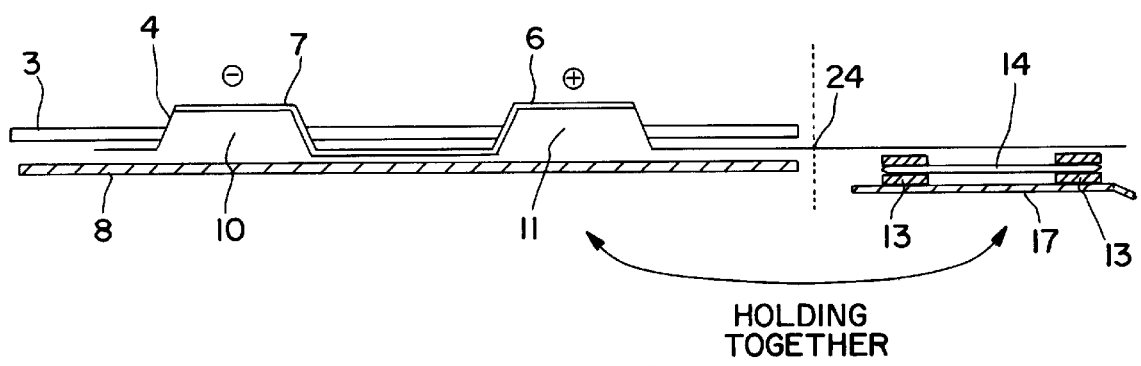

FIG. 18 is a schematic diagram showing an iontophoresis device as a comparative example, in which (a), (b) and (c) are a view of the surface, views of the inner portion and back face and a cross sectional view of the device, respectively. This Comparative Example relates to a device in which an electrode portion and a drug portion are unified through a backing and is designed in such a manner that the electrode portion and the drug portion connected through a hinge are folded at the hinged portion upon application after removing a liner 17 on the electrode portion side to thus assemble the device. In this connection, internal structures of every portions are the same as those discussed above in connection with Examples.

TEST EXAMPLE 1

Determination of Blood Concentration of Salmon Calcitonin

In this Example, the following are newly produced and used in respect of Example 1 and Comparative Example 1: In Example 1 and Comparative Example 1, 1.0 g of a 1.5% agar gel containing a citric acid buffering solution (33 mM, pH 5) was introduced into the conductive layer adjacent to 2.5 cm$^2$ of a silver-printed portion (anode), while 1.0 g of sodium chloride-containing polyvinyl alcohol (UF-250G available from Unitika Ltd.) was introduced into a silver chloride-printed portion (cathode) to form an electrode portion. Moreover, a drug portion was prepared by dropwise addition of 20 IU of salmon calcitonin to 3.46 cm$^2$ of a drug support film (BIODYNE+ available from Nihon PALL Ltd.) and then drying the film.

After assembling the iontophoresis devices provided with the parts thus produced, according to the procedures used in Example 1 and Comparative Example 1, each device was fitted to the abdominal region of an SD rat (body weight: 250 g) and the device was electrically charged by passing an electric current from the current-generating portion at a pulsed, depolarized voltage of 12 V, through a donor electrode as an anode and a reference electrode as a cathode. In this connection, four male persons each assembled the iontophoresis devices of Example 1 and Comparative Example 1. Sera were obtained by intrajugularly collecting blood from the rats with the elapse of time. The concentration of salmon calcitonin in the sera were determined using a radio immunoassay kit (Peninsula Salmon Calcitonin Quantitative Analysis Kit). The results thus obtained are plotted on FIG. 19.

Figure 19:
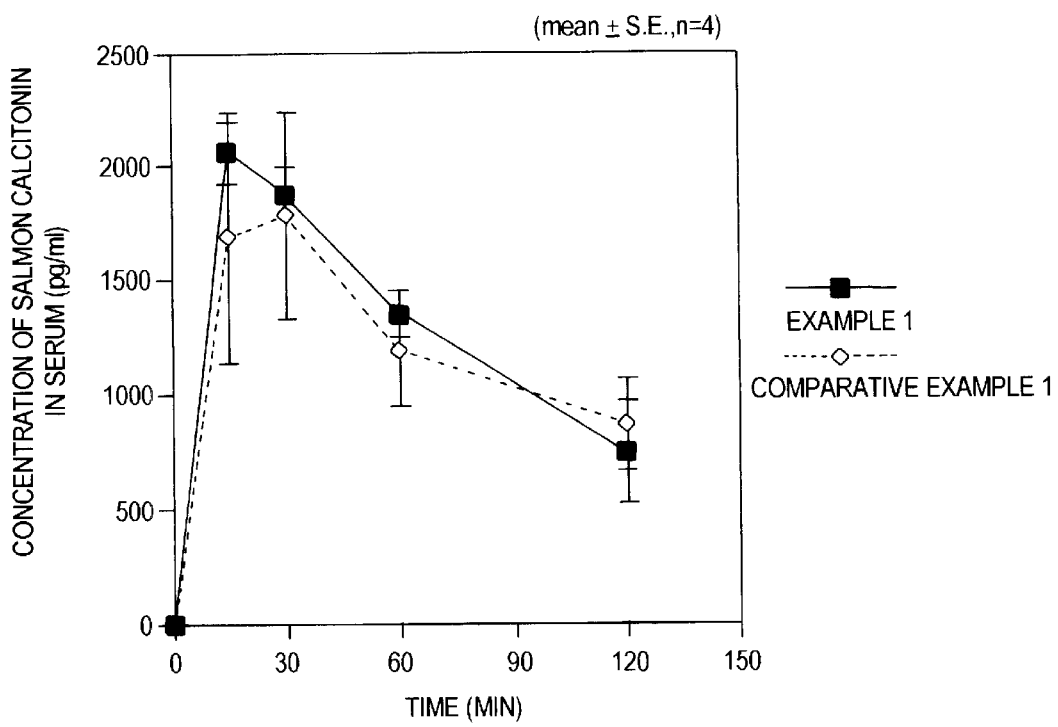
FIG. 19 is a graph showing changes, with time, of salmon calcitonin in the serum observed in Test Example 1.

As will be seen from the results shown in FIG. 19, the blood concentrations of salmon calcitonin observed after 5 minutes were found to be 2056±139 pg/ml (averaged value± standard deviation) for Example 1 and 1867±548 pg/ml, the tendency of the changes in the blood concentration observed for Example 1 and Comparative Example 1 were approximately identical to each other and there was not observed any significant difference therebetween. However, the blood concentration of salmon calcitonin observed for Comparative Example 1 varied widely as compared with that observed for Example 1 and this clearly indicates that the artificial errors upon the assemblage of the devices exert considerable influence on the blood concentration of salmon calcitonin. Consequently, these results clearly indicate that the assembling method of Example 1 makes the assembling operations easy and precise when practically using the device and permits the elimination of any artificial error as much as possible and the precise supply of water required for the dissolution of the drug to the drug support.

TEST EXAMPLE 2

Evaluation of Stability with Time of Salmon Calcitonin Incorporated into Drug Portion The devices of Example 1 and Comparative Example 1 used in Test Example 1 were packaged under the conditions specified in the following Table 1 and allowed to stand at 25° C., 65% RH to thus evaluate the stability, with time, of salmon calcitonin.

TABLE 1

| | Structure of the Content | Drying Agent | Conditions for Allowing to Stand |
|---|---|---|---|
| Example 1 | Drug portion alone | Present | 25° C., 65% RH |
| Comparative Example 1-A | Provided with integrated electrode and drug portions | Present | 25° C., 65% RH |
| Comparative Example 1-B | Provided with integrated electrode and drug portions | Absent | 25° C., 65% RH |

In this Test Example, a composite aluminum packaging material (available from OKADA SHIGYO K.K.) and 1.0 g of a product (available from OZO Chemical Co., Ltd.) were used as the packaging material and the drying agent, respectively. The results thus obtained are plotted on FIG. 20.

Figure 20:
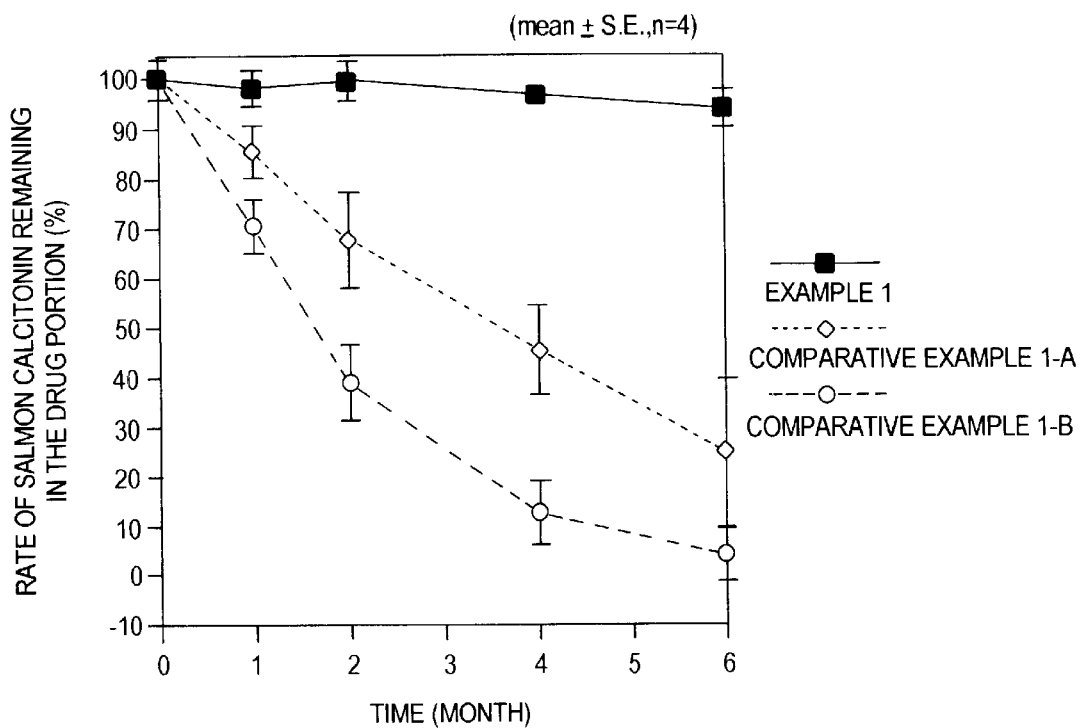
FIG. 20 is a graph showing changes, with time, of the rate of the salmon calcitonin remaining in the drug portion, observed in Test Example 2.

The results plotted on FIG. 20 indicate that, when the water-containing electrode portion and the drug portion in a dried condition are packed in the same package, the former adversely affects the stability, with time, of the drug in the drug portion. In addition, when the electrode and drug portions are packed in the same package and a drying agent is used therein, the drug stability is improved to some extent, but it was found, in one out of four cases, that the water in the electrode portion was exhausted after allowing it to stand over 6 months. On the other hand, the drug exhibited quite excellent stability in the device of Example 1.

From the foregoing, it would be recognized that it is practically difficult to ensure the long-term stability of a drug using a device provided with integrated electrode and drug portions. Moreover, in case of a device provided with electrode and drug portions separated from one another, a drying agent may be used and therefore, the long-term stability of a drug would further be improved.

In addition, the iontophoresis device according to the present invention has technical features described above and therefore, the three portions, i.e., the current-generating portion the drug portion and electrode portion can separately be stored before the operation of the device. For this reason, if a drug having insufficient stability to water (such as physiologically active peptides) is incorporated into the drug portion, it is not feared that the drug is decomposed with time due to the evaporation of water present in the electrode portion provided with the built-in drug-dissolving portion.

Moreover, the device does not require any package for the complete elimination of the evaporation of water originated from the electrode portion and therefore, the device is also advantageous from the economical standpoint. Furthermore, an agent for improving the stability of the drug portion such as drying agent can be used in the device according to the present invention while such an agent cannot be used in case where the drug portion and the electrode portion are united, because of the influence thereof on the drug-dissolving portion and accordingly, the long-term stability of the drug is further improved.

Moreover, the device of the present invention is designed in such a manner that the drug support of the drug portion automatically contacts with the drug-dissolving portion of the electrode portion and the drug present in the drug support is thus activated, by assembling, upon operating the device, the separately stored three portions, i.e., the current-generating portion, the drug portion and the electrode portion with the aid of the conductive snap connector or the auxiliary stand for assemblage such that there is no aberration of position between the electrode and drug portions and by peeling off and pulling out the liner of the drug portion from the device. For this reason, the present invention makes the assembling operations easy and precise when practically using the device and permits the elimination of any artificial error as much as possible and the precise supply of water required for the dissolution of the drug to the drug support.

In addition, the conductive snap connector also serves as a means for electrically connecting the electrode portion to the current-generating portion and therefore, the treatment of a patient can be initiated simply by fitting the device, after the assemblage, to an application site of the patient. The operability of the device would be further improved if using an auxiliary stand for assemblage as a means for helping the application of the device.

From the foregoing, the iontophoresis device according to the present invention exhibits excellent pharmacological effect and permits the achievement of an improved compliance of patients. Moreover, the device can ensure sufficient safety in both operations and functions and thus has high reliability.

Industrial Applicability

The iontophoresis device according to the present invention is effective for ensuring the long-term stability of a drug and the method of assembling the device according to the present invention is advantageous in that the device can easily be assembled. Therefore, the present invention is suitably used for the iontophoresis in the medical field.

What is claimed is:

1. An iontophoresis device comprising a drug-dissolving portion provided with an electrode portion having a first alignment structure and a drug support provided with a drug portion having a second alignment structure, which coincides with the first alignment structure, wherein the drug support contacts with the drug-dissolving portion by coinciding the second alignment structure of the drug portion with the first alignment structure of the electrode portion.

2. The iontophoresis device according to claim 1, wherein the first and second alignment structures are openings formed on the electrode portion and the drug portion, respectively.

3. The iontophoresis device according to claim 1, further comprising a current-generating portion connected to a connecting cord having a fourth alignment structure, which coincides with the first alignment structure of the electrode portion, wherein the connecting cord is coupled to the electrode portion by coinciding the fourth alignment structure of the connecting cord with the first alignment structure of the electrode portion.

4. The iontophoresis device according to claim 1, further comprising a current-generating portion having a third alignment structure, which coincides with the first alignment structure of the electrode portion, wherein the current-generating portion is coupled to the electrode portion by coinciding the third alignment structure of the current-generating portion with the first alignment structure of the electrode portion.

5. The iontophoresis device according to claim 4, wherein the third alignment structure is an electrode terminal formed on the current-generating portion.

6. An iontophoresis device comprising a drug-dissolving portion provided with an electrode portion having a first alignment structure, a current-generating portion having a third alignment structure, which coincides with the first alignment structure and a connector having a fifth alignment structure, which coincides with the first alignment structure, wherein the electrode portion, the current-generating portion and the connector are coupled together while the electrode portion is sandwiched between the current-generating portion and the connector by coinciding the said alignment structures with each other.

7. The iontophoresis device according to claim 6, wherein the alignment structures are constituted by a conductive material.

8. An iontophoresis device comprising a current-generating portion for supplying a driving force for drug-absorption, a drug portion provided with a drug support and an electrode portion provided with a drug-dissolving portion, wherein the electrode portion and the drug portion are arranged while they are in contact and in line with one another by the use of a means for maintaining the arrangement upon operation of the device to thus contact the drug support of the drug portion with the drug-dissolving portion of the electrode portion.

9. The iontophoresis device according to claim 8, wherein at least the drug portion among the current-generating portion, the electrode portion and the drug portion is packed in a separate package.

10. The iontophoresis device as set forth in claim 8, wherein the arrangement-maintaining means serves to mechanically connect the electrode portion to the drug portion and/or to electrically connect the electrode portion to the current-generating portion.

11. The iontophoresis device according to claim 8 wherein the arrangement-maintaining means includes at least one of a current-generating portion, a conductive snap connector and an auxiliary stand for assemblage.

12. An iontophoresis device set at least comprising an electrode portion having a first alignment structure and a drug-dissolving portion; and a drug portion having a second alignment structure, which coincides with the first alignment structure, and a drug support, wherein the drug portion and the electrode portion are separately accommodated.

13. The iontophoresis device set according to claim 12, further comprising a current-generating portion having a third alignment structure, which coincides with the first alignment structure and a connector having a fifth alignment structure, which coincides with the first alignment structure, wherein the drug portion is accommodated independent of the current-generating portion and the connector.

14. The iontophoresis device set according to claim 12, further comprising an auxiliary stand for assemblage having a sixth alignment structure, which coincides with the first alignment structure, wherein the drug portion and the auxiliary stand are separately accommodated.

15. A method of assembling an iontophoresis device, which comprises an electrode portion having an alignment structure and a drug-dissolving portion covered with a cover material; and a drug portion having an alignment structure and a drug support whose both sides are covered with covers, comprising the steps of peeling off the cover material of the electrode portion; coinciding the alignment structures of the electrode and drug portions with each other to thus put the drug support of the drug portion in position on the drug-dissolving portion of the electrode portion; peeling off the cover of the drug support on the side of the drug-dissolving portion; and fixing the drug support to the electrode portion.

16. The method of assembling an iontophoresis device according to claim 15, further comprising a step of peeling off at least part of the cover of the drug support on the side opposite to the drug-dissolving portion.

17. The method of assembling an iontophoresis device according to claim 16, wherein the device is also provided with an auxiliary stand for assemblage having an alignment structure and the alignment structures of the electrode and drug portions coincide with each other using the alignment structure of the auxiliary stand for assemblage.

18. The method of assembling an iontophoresis device according to claim 17, wherein both of the alignment structures of the electrode and drug portions are openings formed on the electrode portion, and the drug portion respectively, and the alignment structure of the auxiliary stand for assemblage is an alignment rod capable of being inserted into the openings.

19. The method of assembling an iontophoresis device according to claim 16, wherein the device is provided with a current-generating portion having an alignment structure and an auxiliary stand for assemblage having an alignment structure and the alignment structures of the electrode and drug portions coincide with each other using the alignment structures of the auxiliary stand for assemblage and the current-generating portion.

20. The method of assembling an iontophoresis device according to claim 19, wherein both of the alignment structures of the electrode and drug portions are openings formed on the electrode and drug portions respectively, the alignment structure of the auxiliary stand for assemblage is a space for accommodating the current-generating portion and the alignment structure of the current-generating portion is an electrode terminal capable of being inserted into the openings.

21. The method of assembling an iontophoresis device according to claim 16, wherein the device is provided with a current-generating portion having an alignment structure, an auxiliary stand for assemblage having an alignment structure and a connector having an alignment structure; the alignment structures of the electrode and drug portions coincide with one another using the three alignment structures of the auxiliary stand for assemblage, the current-generating portion and the connector.

22. The method of assembling an iontophoresis device according to claim 21, wherein both of the alignment structures of the electrode and drug portions are openings formed on the electrode and drug portions respectively, the alignment structure of the auxiliary stand for assemblage is a space for accommodating the connector and the alignment structure of the connector is a connecting member capable of being fixed to the alignment structure of the current-generating portion through the openings of the electrode and drug portions.

23. The method of assembling an iontophoresis device according to claim 15, wherein the device is also provided with an auxiliary stand for assemblage having an alignment structure and the alignment structures of the electrode and drug portions coincide with each other using the alignment structure of the auxiliary stand for assemblage.

24. The method of assembling an iontophoresis device according to claim 23, wherein the both of the alignment structures of the electrode and drug portions are openings formed on the electrode portion and the drug portion respectively and the alignment structure of the auxiliary stand for assemblage is an alignment rod capable of being inserted into the openings.

25. The method of assembling an iontophoresis device according to claim 15, wherein the device is provided with a current-generating portion having an alignment structure and an auxiliary stand for assemblage having an alignment structure and the alignment structures of the electrode and drug portions coincide with each other using the alignment structure of the auxiliary stand for assemblage and the current-generating portion.

26. The method of assembling an iontophoresis device according to claim 25, wherein the both of the alignment structures of the electrode and drug portions are openings formed on the electrode and drug portions respectively, the alignment structure, of the auxiliary stand for assemblage is a space for accommodating the current-generating portion and the alignment structure of the current-generating portion is an electrode terminal capable of being inserted into the openings.

27. The method of assembling an iontophoresis device according to claim 15, wherein the device is provided with a current-generating portion having an alignment structure, an auxiliary stand for assemblage having an alignment structure and a connector having an alignment structure; the alignment structures of the electrode and drug portions coincide with one another using the three alignment structures of the auxiliary stand for assemblage, the current-generating portion and the connector.

28. The method of assembling an iontophoresis device according to claim 27, wherein the both of the alignment structures of the electrode and drug portions are openings formed on the electrode and drug portions respectively, the alignment structure of the auxiliary stand for assemblage is a space for accommodating the connector and the alignment structure of the connector is a connecting member capable of being fixed to the alignment structure of the current-generating portion through the openings of the electrode and drug portions.

29. A method of assembling an iontophoresis device comprising the step of coinciding an alignment structure of an electrode portion with an alignment structure of a drug portion using at least one of alignment structures of an auxiliary stand for assemblage, a current-generating portion and a connector to thus put a drug support of the drug portion in position on a drug-dissolving portion of the electrode portion.

30. The method of assembling an iontophoresis device according to claim 29, wherein the both alignment structures of the electrode and drug portions are openings formed on the electrode and drug portions respectively and at least one of the alignment structures of the auxiliary stand for assemblage, the current-generating portion and the connector is a rod-like member capable of being inserted into the openings.

* * * * *